(12) United States Patent
Clausen et al.

(10) Patent No.: US 7,449,316 B2
(45) Date of Patent: *Nov. 11, 2008

(54) UDP-GALACTOSE: β-D-GALACTOSE-R 4-α-D-GALACTOSYLTRANSFERASE, α4GAL-T1

(75) Inventors: Henrik Clausen, Holte (DK); Eric Paul Bennett, Lyngby (DK); Rudi Steffensen, Pandrup (DK)

(73) Assignee: Glycozym APS, Holte (DK)

( * ) Notice: Subject to any disclaimer, the term of this patent is extended or adjusted under 35 U.S.C. 154(b) by 308 days.

This patent is subject to a terminal disclaimer.

(21) Appl. No.: 11/317,196

(22) Filed: Dec. 22, 2005

(65) Prior Publication Data

US 2006/0099688 A1 May 11, 2006

Related U.S. Application Data

(63) Continuation of application No. 10/217,335, filed on Aug. 9, 2002, now Pat. No. 7,115,404, which is a continuation of application No. PCT/DK01/00087, filed on Feb. 9, 2001.

(60) Provisional application No. 60/182,037, filed on Feb. 11, 2000.

(51) Int. Cl.

| C12N 9/10 | (2006.01) |
|---|---|
| C12P 19/00 | (2006.01) |
| C12P 21/04 | (2006.01) |
| C12Q 1/00 | (2006.01) |
| C12Q 1/68 | (2006.01) |
| C12N 1/20 | (2006.01) |
| C12N 15/00 | (2006.01) |
| C07H 21/04 | (2006.01) |

(52) U.S. Cl. ................. 435/193; 435/4; 435/6; 435/69.1; 435/71.1; 435/252.3; 435/320.1; 435/72; 536/23.2

(58) Field of Classification Search ........... None
See application file for complete search history.

(56) References Cited

U.S. PATENT DOCUMENTS 7,115,404 B2 * 10/2006 Clausen et al. ............. 435/193

FOREIGN PATENT DOCUMENTS

| WO | WO 96 10086 A | 4/1996 |
| WO | WO 01 57190 A2 | 8/2001 |

OTHER PUBLICATIONS

Almeida, R., et al., "A Family of Human β4-Galactosyltransferases: Cloning and expression of two novel UDP-Galactose: β-N-Acetylglucosamine β1, 4-Galactosyltransferases, β4Gal-T2 and β4Gal-T3", *J. Biol. Chem.*, 272:51:31979-31992, 1997.

Amado, M., et al., "Identification and characterization of large galactosyltransferase gene families: galactosyltransferases for all functions", *Biochim. Biophys. Acta in press*, pp. 35-53, 1999.

Bailly, P., et al., "P Blood Group and Related Antigens", Blood Cell Biochemistry, P. Plenum Press,, pp. 299-329, 1995.

Bailly, P., et al., "Biosynthesis of the blood group $P^k$ and $P_1$ antigens by human kidney microsomes", *Carbohydrate Res.*, 228:277-287, 1992.

Bennett, E.P., et al., "cDNA Cloning and Expression of a Novel Human UDP-N-acetyl-α-D-galactrosamine", J. Biol. Chem. 271:29:17006-17012, 1996.

Bennett, E.P., et al., "Cloning of a Human UDP-N-Acetyl-α-D-Galactosamine: Polypeptide-N-Acetylgalactosaminyltransferase That Complements Other GalNAc-Transferases in Complete O-Glycosylation of the MUC1 Tandem Repeat", J. Biol. Chem. 273:46:30472-30481, 1998.

Brew, K., et al., "The Role of α-Lactalbumin and the A Protein in Lactose Synthetase: A Unique Mechanism for the Control of a Biological Reaction" *Proc. Natl. Acad. Sci.* USA, 59:491-497, 1968.

Brodbeck, U., et al., The Isolation and Identification of the B Protein of Lactose Synthetase as "-Lactalbumin", *J. Biol. Chem.*, 242:7:1391-1397, 1967.

Cedergren, B., "Population studies in northern Sweden IV. Frequency of the blood type p", *Hereditas* 73:27-30, 1973.

Charron, M., et al., "The increased level of β1,4-galactosyltransferase required for lactose biosynthesis is achieved in part by translational control", *Proc. Natl. Sci. USA*, 95:14805-14810, 1998.

Clausen, H., et al., "ABH and Related Histo-Blood Group Antigens; Immunochemical Differences in Carrier Isotypes as Their Distribution", *Vox Sang.* 56:1-20, 1989.

Dabrowski, J., et al., "Structural Analysis of Glycosphingolipids by High-Resolution $^1$H Nuclear Magnetic Resonance Spectroscopy", *American Chem. Soc.*, 19:5652-5658, 1980.

Daniels, G.L., et al., "Terminology for Red Cell Surface Antigens", ISBT Working Party Oslo Report, International Society of Blood Transfusion, *Vox Sang.*, 77:52-57, 1997.

(Continued)

*Primary Examiner*—Yong D Pak
(74) *Attorney, Agent, or Firm*—Darby & Darby, P.C.

(57) ABSTRACT

A novel gene defining a novel enzyme UDP-galactose: β-D-galactose-R 4-α-D-galactosyltransferase, termed α4Gal-T1, with unique enzymatic properties is disclosed. The invention provides isolated DNA molecules and DNA constructs encoding α4Gal-T1 and derivatives thereof by way of amino acid deletion, substitution or insertion exhibiting α4Gal-T1 activity, as well as cloning and expression vectors including such DNA, host cells comprising DNA encoding α4Gal-T1, and recombinant methods for providing α4Gal-T1. The enzyme α4Gal-T1 and α4Gal-active derivatives thereof are disclosed. Further, the invention discloses methods of obtaining α1, 4galactosyl glycosylated glycosphingolipids by use of an enzymatically active α4Gal-T1 protein thereof or by using cells stably transfected with a vector including DNA encoding an enzymatically active α4Gal-T1 protein as an expression system for recombinant production of such glycosphingolipids. Also a method for the identification of DNA sequence variations in the α4Gal-T1-coding exon by PCR, and detecting the presence of DNA sequence variation, are disclosed.

11 Claims, 7 Drawing Sheets

OTHER PUBLICATIONS

Do, Ki-Young, et al., "α-Lactalbumin Induces Bovine Milk β-1,4-Galactosyltransferase to Utilize UDP-GalNAc", *J. Biol. Chem.*, 270:18447-18451, 1995.

Fletcher, K.S., "P Blood Group Regulation of Glycosphingolipid Levels in Human Erythrocytes", *J. Biol. Chem.*, 254:22:11196-11198, 1979.

Gotschlich, E.C., "Genetic Locus for the Biosynthesis of the Variable Portion of *Neisseria genorrhoeae* Lipooligosaccharide", *J. Exp. Med.*, 180:2181-2190, 1994.

Iizuka, S, et al., "Studies on the Human Blood Group P System: An existence of UDP-Gal:Lactosylceramide α→1,4 Galactosyltransferase in the Small ρ type cells[1]", *Biochem. Biophys. Res. Commun.*, 37:1187-1195, 1986.

Kannagi, R., et al., "New Globoseries Glycosphingolipids in Human Teratocarcinoma Reactive with the Monoclonal Antibody Directed to a Developmentally Regulated Antigen, Stage-specific Embryonic Antigen 3", *J. Biol. Chem.*, 258:8934-8942, 1983.

Karlsson, K.A., "Meaning and therapeutic potential of microbial recognition of host glycoconjugates", *Molecular Microbiology* 29(1):1-11, 1998.

Kelly, R.J., Ernst, L.K., Larsen, R.D., Bryant, J.G., Robnson, J.S. and Lowe, J.B., Molecular Basis for H blood group deficiency in Bombay (oh) and para-Bombay individuals. *Proc Natl. Acad. Sci.*, U.S.A. 91:5843-5847, 1994.

Kelly R.J., et al., "Sequence and expression of a candidate for the human Secretor blood group alpha (1,2) fucosyltransferase gene (FUT2). Homozygosity for an enzyme-inactivating nonsense mutation commonly correlates with the non-secretor phenotype", *J. Biol. Chem.* 270:4640-4649, 1995.

Keusch, J., et al., "Cloning of $Gb_3$ Synthase, the Key Enzyme in Globo-series Glycosphingolipid Synthesis, Predicts a Family of α1,4-Glycosyltransferases Conserved in Plants, Insects, and Mammals", J. Biol. Chem., 275:33:25315-25321, Aug. 2000.

Kojima, Yoshinao, et al., "Molecular Cloning of Globotriaosylceramide/CD77 Synthase, a Glycosyltransferase That Initiates the Synthesis of Globo Series Glycosphingolipids", J. Biol. Chem. 275:20:15152-15156, XP002901746, (May 2000).

Kozak, M., Structural features in eukaryotic mRNAs that modulate the initiation of translation, *J. Biol. Chem.* 266:19867-19870, 1991.

Landsteiner, K., et al., "Further Observations on Individual Differences of Human Blood", *Proc. Soc. Biol. Exp. Biol. N.Y.*, 24:941-942.

Lopez, M., et al., "Characterization of a UDP-Gal:Galβ1-3GalNAc α1,4-Galactosyltransferase Activity in a *Mamestra brassicae* Cell Line", *J. Biol. Chem.* 273:50:33644-33651, 1998.

Mandell, U., et al., "Expression of polypeptide GalNAc-transferases in stratified epithelia and squamous cell carcinomas: immunohistological evaluation using monoclonal antibodies to three members of the GalNAc-transferase family", *Glycobiology*, 9:1:43-52, 1999.

Mangeney, M., et al., "Apoptosis induced in Burkitt's lymphoma cells via gb3/CD77, a glycolipid antigen", *Cancer Res.* 53:5314-5319, 1993.

Marcus, D.M., et al., "The Ii and P Blood Group Systems", *Immunol. Ser.*, 43:701-712, 1989.

Marcus, D.M., et al., "Immunochemistry of the P Blood Group System", *Prog. Clin. Bliol. Res.*, 43:55-65, 1980.

Martin, S.L., et al., "Lewis X Biosynthesis in Helicobacter pylori", *J. Biol. Chem.*, 272:34:21349-21356, 1997.

McAlpine, P.J, et al., "Is the $DIA_1$ locus linked to the P blood group locus? Cytogenet", *Cell Genet.* 22:629-632, 1978.

Mollicone, R., et al., Molecular Basis for Lewis α (1,3/1,4)-Fucosyltransferase Gene Deficiency (FUT3) Found in Lewis-negative Indonesian Pedigrees, *J. Biol. Chem.*, 269:33:20987-20994, 1994.

Naiki, M., et al., "Structure of the Human Erythrocyte Blood Group $P_1$ glycosphingolipid", Biochemistry 14:4831-4837, 1975.

Naiki, M., et al., "The Human Erythricyte P and $P^k$ Blood Group Antigens: Identification as Glycosphingolipids", *Biochem. Biophys. Res. Commn.*, 60:1105-1111, 1974.

Nakayama, J., et al., "Expression cloning of a human α1,4-N-acetylglucosaminyltransferase that forms GlcNαc1→6Galβ→R, a glycan specifically expressed in the gastric gland mucous cell-type mucin", *Proc. Natl. Acad. Sci.*, 96:8991-8996, 1999.

Nishihara, S., et al., "Molecular Genetic Analysis of the Human Lewis Histo-blood Group System", *J. Biol. Chem.*, 269:46: 29271-29278, 1994.

Paulson, J.C., et al., "Glycosyltransferases", *J. Biol. Chem.*, 264: 30:17615-17618, 1999.

Puri, A., et al., "Role of Glycosphingolipids in HIV-1 Entry: Requirement of Globotriosylceramide (Gb3) in CD4/CXCR4-depednent Fusion", *Bioscience Reports*, 19:4:317-325, 1999.

Sasaki, K., et al., Expression cloning of cDNA encoding a human beta-1,3-N-acetylglucosaminyltransferase that is essential for poly-N-acetyllactosamine synthesis. *Proc. Natl. Acad. Sci.*, U.S.A., 94:14294-14299, 1997.

Steffensen, Rudi, et al., "Cloning and Expression of the Histo-blood pk UDP-galactose: Galβ1-4Glcβ1-Cer α1,4-Galactosyltransferase", *J. Biol. Chem.*, 275:22:6723-16729, XPO02901745, Jun. 2000.

Taga, S., et al., "Intracellular Signaling Events in CD77-Mediated Apoptosis of Burkitt's Lymphoma Cells", *Blood*, 90:7:2757-2767, 1997.

Taga S., et al., "Sequential changes in glycolipid expression during human cell differentiation: enzymatic bases", *Biochim Biophys. Acta.*, 1254:56-65, 1995b.

Taga, S., et al., "Differential Regulation of Glycosphingolipid Biosynthesis in Phenotypically Distinct Burkitt's Lymphoma Cell Lines", *Int. J. Cancer*, 61:261-267, 1995.

Tippett, P., et al., "Red Cell Antigens P (Globoside) and Luke: Identification by Monoclonal Antibodies Defining the Murine Stage-Specific Embryonic Antigens -3 and -4 (SSEA-3 and SSEA-4)[1]", *Vox Sang*, 51:53-56, 1996.

Wakarchuk, W., et al., "Role of paired basic residues in the expression of active recombinant galactosyltransferases from the bacterial pathogen *Neisseria meningitidis*", *Protein Engineering*, 11:4:295-302, 1998.

Watkins, W.M., "Biochemistry and Genetics of the ABO, Lewis, and P Blood Group Systems", *Adv. Hum. Genet.*, 10:1-136, 1980.

Wiels, J., "CD77 Workshop Panel Report", *Garland Publishing Inc.* 175-177, 1997.

Wiels, J., "Histo-blood group p:biosynthesis of globoseries glycolipids in EBV-transformed B cell lines", *Glycoconj. J.*, 13:529-535, 1996.

Yamamoto, F., et al., "Molecular genetic basis of the histo-blood group ABO system", *Nature*, 345:229-233, 1990.

Yoshida, H., et al., "Removal of maternal antibodies from a woman with repeated fetal loss due to P blood group incompatibility", *Transfusion*, 34:702-705, 1994.

Wiggins, et al. "Activity of the yeast MNN1lfa-1,3-mannosyltransferase requires a motif conserved in many other families of glycosyltransferases" *Proc. Natl. Acad. Sci.*, U.S.A., 95:7945-7950, 1998.

Zhou, D., et al., A beta-1,3-N-acetylglucosaminyltransferase with poly-N-acetyllactosamine synthase activity is structurally related to beta-1,3-galactosyltransferases. *Proc Natl. Acad. Sci.*, U.S.A., 96:406-411, 1999.

\* cited by examiner pk α4Gal-T

```
         HCRS131
    1    ATGTCCAAGCCCCCCGACCTCCTGCTCCGGCTGCTCCGGGGCCCCAAGGCAGCGGGGTCTGCACCCTGTTCATGATGGCTTCAAGTTCAGTTTTTCGTCTCCATCATGATCTACTGG    120
    1    M  S  K  P  P  D  L  L  L  R  L  L  R  G  A  P  R  Q  R  Y  C  T  L  F  I  I  G  E  K  F  F  F  V  S  I  M  I  Y  W     40
                                                   HCRS124
  121    CACGTTGTGGGAGAGCCCAAGGAGAAGGGCAGCTCTATAACCTGCCAGCAGAGAATCCCCGCCGAGATCCCCTGCCCCACCCTGACACCCCCACCCAGCCACGGCCCCACTCCAGGCAACATCTTC    240
   41    H  V  V  G  E  P  K  E  K  G  Q  L  Y  N  L  P  A  E  I  P  C  P  T  L  T  P  P  P  S  H  G  P  T  P  G  N  I  F     80
         .....
  241    TTCCTGGAGACTTCAGACCGGACCAACCCCAACTTCCTGTTCATGTGCTCTGGTGGAGTGCCGCAGAACTCACCCGAATCCACGTGCTGGTCCTGATGAAGGGCTTCGGGTGGCC    360
   81    F  L  E  T  S  D  R  T  N  P  N  F  L  F  M  C  S  V  E  S  A  A  R  T  H  P  E  S  H  V  L  V  L  M  K  G  L  P  G  G    120

361    AACGCCCTCTCTGCCCGGAGGCATTGGGGCATCTCACTTCTGAGTTGCTTCCCCGAATGTCCAGGATGCTCCGCTGCGGGAGCTGCTTCCGAGACACCCCCGCTGGCCGACTGGTACGCG    480
  121    N  A  S  L  P  R  R  H  L  G  I  S  L  L  S  C  F  P  N  V  Q  M  L  P  L  D  L  R  E  L  F  R  D  T  P  L  A  D  W  Y  A    160

481    GCCCTGCAGGGGCGCTGGGAGCCCTACCTCCTGCCCGTGCTGTCCCGCTACGTCGGGCACCAGAGTCCTCATGTGGAAGTTCGGGGGCATCTACCTGGACACGGACTTCATTGTTCTCAAGAAC    600
  161    A  V  Q  G  R  W  E  P  Y  L  L  P  V  L  S  D  A  S  R  I  A  L  M  W  K  F  G  G  I  Y  L  D  T  D  F  I  V  L  K  N    200

601    CTGCGGAACCTGACCAACGTGCTGGGCACCCAGTCTCGGGCGCTACGTCCTCCGACTCCTCAACGGCGCCTTCCTGGCCTTCGAGCGCCGGCACGAGTTCATGGCCCTGTGCATGCGCGACTTCGTGGACCAC    720
  201    L  R  N* L  T  N  V  L  G  T  Q  S  R  Y  V  L  N  G  A  F  L  A  F  E  R  R  H  E  F  M  A  L  C  M  R  D  F  V  D  H    240

721    TACAACGGCTGGATCTGGGGTCACCAGGGTCCCCAGCTGCTCACCCGGGTCTTCAAGAAGTGGTGCTCCATCCGGAGCCTGGCCGAGAGCCGGGCGTGCCGCGGCGTCACCACCCTGCCC    840
  241    Y  N  G  W  I  W  G  H  Q  G  P  Q  L  L  T  R  V  F  K  K  W  C  S  I  R  S  L  A  E  S  R  A  C  R  G  V  T  T  L  P    280

841    CCTGAGGCCTTCTACCCTCCCATCCCCTGGCAGGATGGGAAGAAGTACTTTGAGGACATCAACCCCGAGGAGCTGCCTCGGTCGCCTGCTCAGTCGCCACCTATGCTGCTGTCTGGAACAAGAAG    960
  281    P  E  A  F  Y  P  P  I  P  W  Q  D  W  K  K  Y  F  E  D  I  N  P  E  E  L  P  R  R  L  L  S  A  T  Y  A  V  H  V  W  N  K  K    320

961    AGCCAGGGCACGCGGTTCGAGGCCACGTCCAGGGCACTGCTGGCCCAGCTGCATGCCCGCTACTGCCCCACGACGCACGAGGCCATGAAAATGTACTTGTGAGGGGCCCGCCAGGTCACC    1080
  321    S  Q  G  T  R  F  E  A  T  S  R  A  L  L  A  Q  L  H  A  R  Y  C  P  T  T  H  E  A  M  K  M  Y  L  *                    353
                                                                                       HCRS131

TCCCCAACCTGCTCCTGATGGGGCCACTGGGCCCCCCTTCCCGGGAGCCAGATTGAGGGCCCGAGCTGCCACCGGAGGAGCCCTTAGGCAGGCTGTGTTGAGGAGCTGTGG
         AGCAGGCCCCAGTGGGAGGCTGTGACACCGGGACACAGTGTTCCTGTCTCGAGGCACAGTGTCCCATAGCCAGGAGGGCTGCAGCCGGAGGCATGTGCCACCGGGCCTTCTAGACA
         ACAGGCCAGGAGGATGAACCTCAGGGCACCCAGGTGGCCAGAAAGCCAGCAGTTGGGACACATGAGTTGCCCAGGTGGGAGGCAGTTGCACCACGAGGTGCCTAAGGGAGGACAAGA
         TTCCCAGAGAGGAGGAGGTCAACAGGAGGTCAGTGGGGACAGGAGCCCAGAGGTGCCACCCCAGCCGCCCTTCTGCCACCCCATCCTTCTTCCCTCCCAGAGATGCCAGG
         GGGTGGGGGGAGGTCTATGCTCTGCCCCTTCCCTCAGACAGGGGCTGGGTGGGGAGGGAGCTCTCCCTCTTTAGGCTCAGGAGAAGCATTTTAAGAAACCCCACCCTGGGCCGCCCCGCAGG
         GGGGCGGTGTATAGATAGCATTATAAACACAGGAGAA
         TAATCAATAGAATAAA
```

FIG. 1

```
α4Gal-T1    : MSKPPDLLLRLLRGAPRQRVCTLFIIGFKTFFVSIMIYWHVVGEPKEKGQLYNLPAEIPCPTLTPPTP      : 69
α4GlcNAc-T  : MRKELQLSLS------VTLLVCGFLYQFTL----------KSS-CLFCLPSEKSHQGLEALLS      : 47

α4Gal-T1    : PSHGPTPGNIFFLETSDFTNPNFLFMCSVESAARTHPESHVLVLMKGLPGGN--ASLPRHLGISLLSCF    : 136
α4GlcNAc-T  : HRRG-----IVFLETSERMEPPHIVSCSVESAAKIYPEWPVVFFMKGLTDSTPMPSNSTYPAFSFLSAI   : 111

DxD
                                                 K
α4Gal-T1    : PNVQMLPLDLRELEFRDTPLADWYAAVQGRWEPYLLPVLSDASRIALMWKFGGIYLDTDFIVLKNLRNLT  : 205
α4GlcNAc-T  : DNVFLFPLDMKRLLEDTPLFSWYNQINASAERNWLHISSDASRLAIIWKYGGIYMDTDVISIRPIPEEN   : 180

*
α4Gal-T1    : NVLGTQSRYVLNGAFLAFERRHEFMALCMRDFVDHYNGWIWGHQGPQLLTRVFKKWCSIRSLAES--RA   : 272
α4GlcNAc-T  : FLAAQASRYSSNGIFG-FLPHHPELWECMENFVEHYNSAIWGNQGPELMTRMLRVWCKLEDFQEVSDLR   : 248

*
α4Gal-T1    : CRGVTTLPFEAFYPIPWQDWKKYFEDINPEELPRLLSATYAVHVWNKKS--QGTRFEATSRALLAQEHA   : 339
α4GlcNAc-T  : CLNISFLHPQRFYPISYREWRRYYEWDTEPS---FNVSYALHLNHHMNQEGRAVIRGSNTLVENLYR    : 314
  *
α4Gal-T1    : RYCPTTHEAMKMYL                                                         : 353
α4GlcNAc-T  : KHCPRTYRDLIKGPEGSVTGELGPGNK                                            : 341

FIG. 2
```

UDP-GALACTOSE: β-D-GALACTOSE-R 4-α-D-GALACTOSYLTRANSFERASE, α4GAL-T1

This is a continuation of application U.S. Ser. No. 10/217,335, filed Aug. 9, 2002, now U.S. Pat. No. 7,115,404, which is a continuation of PCT/DK01/00087, filed on Feb. 9, 2001, which claims priority to U.S. provisional application 60/182,037, filed Feb. 11, 2000. Each of these prior applications is hereby incorporated by reference, in its entirety.

TECHNICAL FIELD

The present invention relates generally to the biosynthesis of glycans found as free oligosaccharides or covalently bound to proteins and glycosphingolipids. This invention is more particularly related to nucleic acids encoding an UDP-D-galactose: β-D-galactose-R 4-α-D-galacto-syltransferase (α4Gal-transferase), which add galactose to the hydroxy group at carbon 4 of D-galactose (Gal). This invention is more particularly related to a gene encoding the blood group $P^k$ (Gb3) synthase, termed α4Gal-T1, probes to the DNA encoding α4Gal-T1, DNA constructs comprising DNA encoding α4Gal-T1, recombinant plasmids and recombinant methods for producing α4Gal-T1, recombinant methods for stably transfecting cells for expression of α4Gal-T1, and methods for identification of DNA polymorphism in patients.

BACKGROUND OF THE INVENTION

The P histo-blood group system is the last of the known carbohydrate defined blood group systems for which the molecular genetic basis has not yet been clarified. The P blood group system involves two major blood group pheno-types, $P_1+$ and $P_1-$ with approximate frequencies of 80 and 20%, respectively (Landsteiner and Levine, 1927; Daniels et al., 1999). $P_1-$ individuals normally express the P antigen ($P_1-$ is designated $P_2$ when P antigen expression is demonstrated), but the rare Pk phenotype lacks the P antigen, while the rare p phenotype lack both P and $P^k$ antigens (for reviews see (Watkins, 1980; Marcus, 1989; Marcus and Kundu, 1980; Issitt and Anstee, 1998; Bailly and Bouhors, 1995)). The $P_1+$ phenotype is defined by expression of the neolacto-series glycosphingolipid $P_1$ (for structures see Table I) (Naiki et al., 1975).

In contrast, the P, $P^k$, and p antigens constitute intermediate steps in biosynthesis of globo-series glycolipids and give rise to $P_1^k$, $P_2^k$, and p phenotypes (Naiki and Marcus, 1974). While the rare $^{Pk}$ phenotype show the same frequency of P1 antigen expression as individuals expressing the P antigen, the p phenotype is always associated with lack of $P_1$ antigen expression. Extensive studies of the chemistry, biosynthesis, and genetics of the P blood group system identified the antigens as being exclusively found on glycolipids, with the blood group specificity being synthesized by at least two distinct glycosyltransferase activities; UDP-galactose: β-D-galactosyl-β1-R 4-α-D-galactosyltransferase (α4Gal-T) activity(ies) for Pk and P1 syntheses and UDP-GalNAc: Gb3 3-β-N-acetylgalactosaminyltransferase activity (EC 2.4.1.79) for P synthesis [for reviews see (Issitt and Anstee, 1998; Bailly and Bouhors, 1995)]. At least two independent gene loci, P and $P_1P^k$, are involved in defining these antigens. The P blood group associated LKE antigen shown to be the extended sialylated Gal-globoside structure (Tippett et al., 1986), may involve polymorphism in an α2,3sialyltransferase activity.

A longstanding controversy has been whether a single or two independent α1,4galactosyltransferases catalyze the synthesis of the $P_1$ neolacto-series glycolipid antigen and the $P^k$ globo-series structure (Watkins, 1980; Marcus, 1989; Marcus and Kundu, 1980; Issitt and Anstee, 1998; Bailly and Bouhors, 1995). Several hypotheses have been proposed, including: i) a model with two distinct functional genes being allelic or non-allelic, where the $P_1$ gene encodes a broadly active α4Gal-T, the $P^k$ gene encodes a restricted α4Gal-T, and a null allele encodes a non-functional protein; ii) a model with two distinct non-allelic genes, where $P_1$ encodes an α4Gal-T that can only synthesize $P_1$ structures and the $P^k$ encodes an α4Gal-T that only synthesize the $P^k$ structure; and iii) a model where one gene locus encodes an α4Gal-T that is modulated by an independent polymorphic gene product to synthesize both $P_1$ and $P^k$ structures. Bailly et al. (Bailly et al., 1992) reported that kidney microsomal α4Gal-T activity from $P_1$ individuals does not compete for the two substrates used by $P_1$ and $P^k$ α4Gal-T activities, and no accumulative effect in $P_1$ synthase activity was observed when mixing microsomal fractions from individuals of $P_1$ and $p^k$ groups. Based on this Bailly and colleagues suggested the existence of two distinct genes, coding for one $P_1$ α4Gal-T with exclusive activity for neolacto-series substrates and one $P^k$ α4Gal-T with exclusive activity for the globo-series substrate. Since p individuals lack the $P_1$ antigen this model inferred that two independent genetic events inactivating both genes was responsible for the p phenotype.

TABLE I

Structures of glycosphingolipids referred to in this study[a]

| Structure | | P blood group antigen |
|---|---|---|
| CDH, LacCer | Galβ1-4Glcβ1-1Cer | p |
| CTH, Gb₃ | Galα1-4Galβ1-4Glcβ1-1Cer | $P^k$ |
| Globoside | GalNAcβ1-3Galα1-4Galβ1-4Glcβ1-1Cer | P |
| Sialyl-Gal-Globoside | NeuAcα2-3Galβ1-3GalNAcβ1-3Galα1-4Galβ1-4Glcβ1-1Cer | LKE |
| Paragloboside, PG | Galβ1-4GlcNAcβ1-3Galβ1-4Glcβ1-1Cer | |
| P₁ | Galα1-4Galβ1-4GlcNAcβ1-3Galβ1-4Glcβ1-1Cer | $P_1$ |

[a]Key: CDH, ceramide dihexoside (lactosylceramide, LacCer); CTH, ceramide trihexoside (Gb₃, globotriaosylceramide); globoside, Gb₄ (globotetraosylceramide); Cer, ceramide; Gal, D-galactose; Glc, D-glucose; GalNAc, N-acetyl-D-galactosamine; GlcNAc, N-acetyl-D-glucosamine; NeuAc, N-acetylneuraminic acid.

Several approaches to gain insight into the P blood group α4Gal-T gene(s) have been attempted. Purification of the mammalian enzymes has not been successful, but identification and cloning of a bacterial α4Gal-T involved in lipopolysaccharide biosynthesis (Gotschlich, 1994; Wakarchuk et al., 1998) potentially provided a strategy to clone the mammalian genes using sequence similarity. Previously, a bacterial α3fucosyltransferase was identified in *helicobactor pylori* using a short sequence motif conserved among mammalian α3fucosyltransferases (Martin et al., 1997). BLAST analysis of gene databases with the coding region of the α4Gal-T gene from *Neisseria Meningococcae* resulted in identification of two human genes encoding putative type II transmembrane proteins with low sequence similarity to the bacterial gene[1]. The genes have open reading frames encoding 349 (EST cluster Hs.251809) and 371 (EST cluster Hs.82837) amino acid residues, and are located at 8q24 and 3p21.1, respectively. Previously, we established Epstein-Barr virus transformed B cells from two p individuals (Wiels et al., 1996). Only the gene at 3p21.1 was found to be expressed in the EBV-transformed p cells, as well as in Ramos cells known to have high Pk α4Gal-T activity. Sequencing of the coding region of the gene showed no mutations in p cells. Finally, expression of full coding or truncated, secreted constructs of either gene in insect cells failed to demonstrate glycosyltransferase activity with a large panel of substrates, including lactosylceramide, for $P^k$ α4Gal-T activity.

[1] R. Steffensen, J. Wiels, E. P. Bennett, and H. Clausen, unpublished observation.

Access to the Pk α4Gal-transferase gene would allow production of efficient enzymes for use in galactosylation of glycosphingolipids, oligosaccharides, and glycoproteins. Such enzymes could be used, for example, in pharmaceutical or other commercial applications that require enzymatic galactosylation of these or other substrates in order to produce appropriately glycosylated glycoconjugates having particular enzymatic, immunogenic, or other biological and/or physical properties. The P blood group system is implicated in important biological phenomena. Blood group p individuals have strong anti-$P_1PP^k$ IgG antibodies and these are implicated in high incidence of spontaneous abortions (Yoshida et al., 1994). The globoseries glycolipid antigens constitute major receptors for microbial pathogens with the Galα1-4Gal linkage being an essential part of the receptor site (for a review see (Karlsson, 1998)). The $P^k$ glycolipid is the CD77 antigen, a B cell differentiation antigen, which is able to transduce a signal leading to apoptosis of the cells (Mangeney et al., 1993). Furthermore, the association of this glycolipid with the type I interferon receptor or with the HIV-1 co-receptor, CXCR4, seems to be crucial for the functions of these receptors (Taga et al., 1997; Puri et al., 1999). Cloning of the $P^k$ synthase is an important step toward understanding the biological roles of the globo-series class of glycolipids, and a first step in elucidating the molecular genetics of the P blood group system. Availability of the $P^k$ synthase gene is important for elucidating the many biological roles of the globo-series class of glycolipids, and may offer new avenues for diagnostic and therapeutic measures. Consequently, there exists a need in the art for UDP-galactose: β-D-galactose-R 4-α-D-galactosyltransferase and the primary structure of the gene encoding this enzyme. The present invention meets this need, and further presents other related advantages, as described in detail below.

SUMMARY OF THE INVENTION

The present invention provides isolated nucleic acids encoding human UDP-galactose: β-D-galactose-R 4-α-D-galacto-syltransferase (α4Gal-T1), including cDNA and genomic DNA. α4Gal-T1 represents the first cloned and expressed eukaryote α4Gal-T gene. The complete nucleotide sequence of αGal-T1, is set forth in SEQ ID NO:10 and FIG. 1.

Variations in one or more nucleotides may exist among individuals within a population due to natural allelic variation. Any and all such nucleic acid variations are within the scope of the invention. DNA sequence polymorphisms may also occur which lead to changes in the amino acid sequence of a α4Gal-T1 polypeptide. These amino acid polymorphisms are also within the scope of the present invention. In addition, species variations i.e. variations in nucleotide sequence naturally occurring among different species, are within the scope of the invention.

In one aspect, the invention encompasses isolated nucleic acids comprising the nucleotide sequence of nucleotides 1-1059 as set forth in FIG. 1 or sequence-conservative or function-conservative variants thereof. Also provided are isolated nucleic acids hybridizable with nucleic acids having the sequence as set forth in FIG. 1 or fragments thereof or sequence-conservative or function-conservative variants thereof; preferably, the nucleic acids are hybridizable with α4Gal-T1 sequences under conditions of intermediate stringency, and, most preferably, under conditions of high stringency. In one embodiment, the DNA sequence encodes the amino acid sequence, as set forth in FIG. 1, from methionine (amino acid no. 1) to leucine (amino acid no. 355).

In a related aspect, the invention provides nucleic acid vectors comprising α4Gal-T1 DNA sequences, including but not limited to those vectors in which the α4Gal-T1 DNA sequence is operably linked to a transcriptional regulatory element, with or without a polyadenylation sequence. Cells comprising these vectors are also provided, including without limitation transiently and stably expressing cells. Viruses, including bacteriophages, comprising α4Gal-T1-derived DNA sequences are also provided. The invention also encompasses methods for producing α4Gal-T1 polypeptides. Cell-based methods include without limitation those comprising: introducing into a host cell an isolated DNA molecule encoding α4Gal-T1, or a DNA construct comprising a DNA sequence encoding α4Gal-T1; growing the host cell under conditions suitable for α4Gal-T1 expression; and isolating α4Gal-T1 produced by the host cell. A method for generating a host cell with de novo stable expression of α4Gal-T1 comprises: introducing into a host cell an isolated DNA molecule encoding α4Gal-T1 or an enzymatically active fragment thereof (such as, for example, a polypeptide comprising amino acids 38-355 as set forth in FIG. 1), or a DNA construct comprising a DNA sequence encoding α4Gal-T1 or an enzymatically active fragment thereof; selecting and growing host cells in an appropriate medium; and identifying stably transfected cells expressing α4Gal-T1. The stably transfected cells may be used for the production of α4Gal-T1 enzyme for use as a catalyst and for recombinant production of peptides or proteins with appropriate galactosylation. For example, eukaryotic cells, whether normal or diseased cells, having their glycosylation pattern modified by stable transfection as above, or components of such cells, may be used to deliver specific glycoforms of glycopeptides and glycoproteins, such as, for example, as immunogens for vaccination.

In yet another aspect, the invention provides isolated α4Gal-T1 polypeptides, including without limitation polypeptides having the sequence set forth in FIG. 1, polypeptides having the sequence of amino acids 38-355 as set forth in FIG. 1, and a fusion polypeptide consisting of at least amino acids 38-355 as set forth in FIG. 1 fused in frame to a second sequence, which may be any sequence that is compatible with retention of α4Gal-T1 enzymatic activity in the fusion polypeptide. Suitable second sequences include without limitation those comprising an affinity ligand or a reactive group.

In another aspect of the present invention, methods are disclosed for screening for mutations in the coding region (exon I) of the α4Gal-T1 gene using genomic DNA isolated from, e.g., blood cells of patients. In one embodiment, the method comprises: isolation of DNA from a patient; PCR amplification of coding exon I; DNA sequencing of amplified exon DNA fragments and establishing therefrom potential structural defects of the α4Gal-T1 associated with P blood groups and disease.

In accordance with an aspect of the invention there is provided a method of, and products for (i.e. kits), diagnosing and monitoring conditions mediated by α4Gal-T1 by determining the presence of nucleic acid molecules and polypeptides of the invention.

Still further the invention provides a method for evaluating a test compound for its ability to modulate the biological activity of a α4Gal-T1 polypeptide of the invention. For example, a substance that inhibits or enhances the catalytic activity of a α4Gal-T1 polypeptide may be evaluated. "Modulate" refers to a change or an alteration in the biological activity of a polypeptide of the invention. Modulation may be an increase or a decrease in activity, a change in characteristics, or any other change in the biological, functional, or immunological properties of the polypeptide. Compounds which modulate the biological activity of a polypeptide of the invention may also be identified using the methods of the invention by comparing the pattern and level of expression of a nucleic acid molecule or polypeptide of the invention in biological samples, tissues and cells, in the presence, and in the absence of the compounds.

In an embodiment of the invention a method is provided for screening a compound for effectiveness as an antagonist of a polypeptide of the invention, comprising the steps of a) contacting a sample containing said polypeptide with a compound, under conditions wherein antagonist activity of said polypeptide can be detected, and b) detecting antagonist activity in the sample. Methods are also contemplated that identify compounds or substances (e.g. polypeptides), which interact with α4Gal-T1 nucleic acid regulatory sequences (e.g. promoter sequences, enhancer sequences, negative modulator sequences). The nucleic acids, polypeptides, and substances and compounds identified using the methods of the invention, may be used to modulate the biological activity of a α4Gal-T1 polypeptide of the invention, and they may be used in the treatment of conditions mediated by α4Gal-T1 such as proliferative diseases including cancer, and thymus-related disorders.

Accordingly, the nucleic acids, polypeptides, substances and compounds may be formulated into compositions for administration to individuals suffering from one or more of these conditions. Therefore, the present invention also relates to a composition comprising one or more of a polypeptide, nucleic acid molecule, or substance or compound identified using the methods of the invention, and a pharmaceutically acceptable carrier, excipient or diluent. A method for treating or preventing these conditions is also provided comprising administering to a patient in need thereof, a composition of the invention. The present invention in another aspect provides means necessary for production of gene-based therapies directed at the thymus. These therapeutic agents may take the form of polynucleotides comprising all or a portion of a nucleic acid of the invention comprising a regulatory sequence of a α4Gal-T1 nucleic acid placed in appropriate vectors or delivered to target cells in more direct ways. Having provided a novel α4Gal-T1, and nucleic acids encoding same, the invention accordingly further provides methods for preparing oligosaccharides. In specific embodiments, the invention relates to a method for preparing an oligosaccharide comprising contacting a reaction mixture comprising a donor substrate, and an acceptor substrate in the presence of a α4Gal-T1 polypeptide of the invention. In accordance with a further aspect of the invention, there are provided processes for utilizing polypeptides or nucleic acid molecules, for in vitro purposes related to scientific research, synthesis of DNA, and manufacture of vectors.

These and other aspects of the present invention will become evident upon reference to the following detailed description and drawings.

BRIEF DESCRIPTION OF THE DRAWINGS

FIG. 1 depicts the DNA sequence (SEQ ID NO:10) and predicted amino acid sequence of human α4Gal-T1 (SEQ ID NO:11). The amino acid sequence is shown in single-letter codes. The hydrophobic segment representing the putative transmembrane domain is underlined with a double line (Kyte & Doolittle, window of 8 (Paulson and Colley, 1989)). One consensus motif for N-glycosylation is indicated by asterisks. The location of the primers used for preparation of the expression constructs are indicated by single underlining. A potential polyadenylation signal is indicated in boldface underlined type.

FIG. 2 is an illustration of multiple sequence analysis (ClustalW) of human α4Gal-T1 (SEQ ID NO: 11) and α4GlcNAc-T (SEQ ID NO: 12). Introduced gaps are shown as hyphens, and aligned identical residues are black boxed. The two amino acid substitutions (M37V and M183K) are indicated above the α4Gal-T1 sequence. Conserved cysteine residues are shown by asterisks.

DETAILED DESCRIPTION OF THE INVENTION

Figure 3:
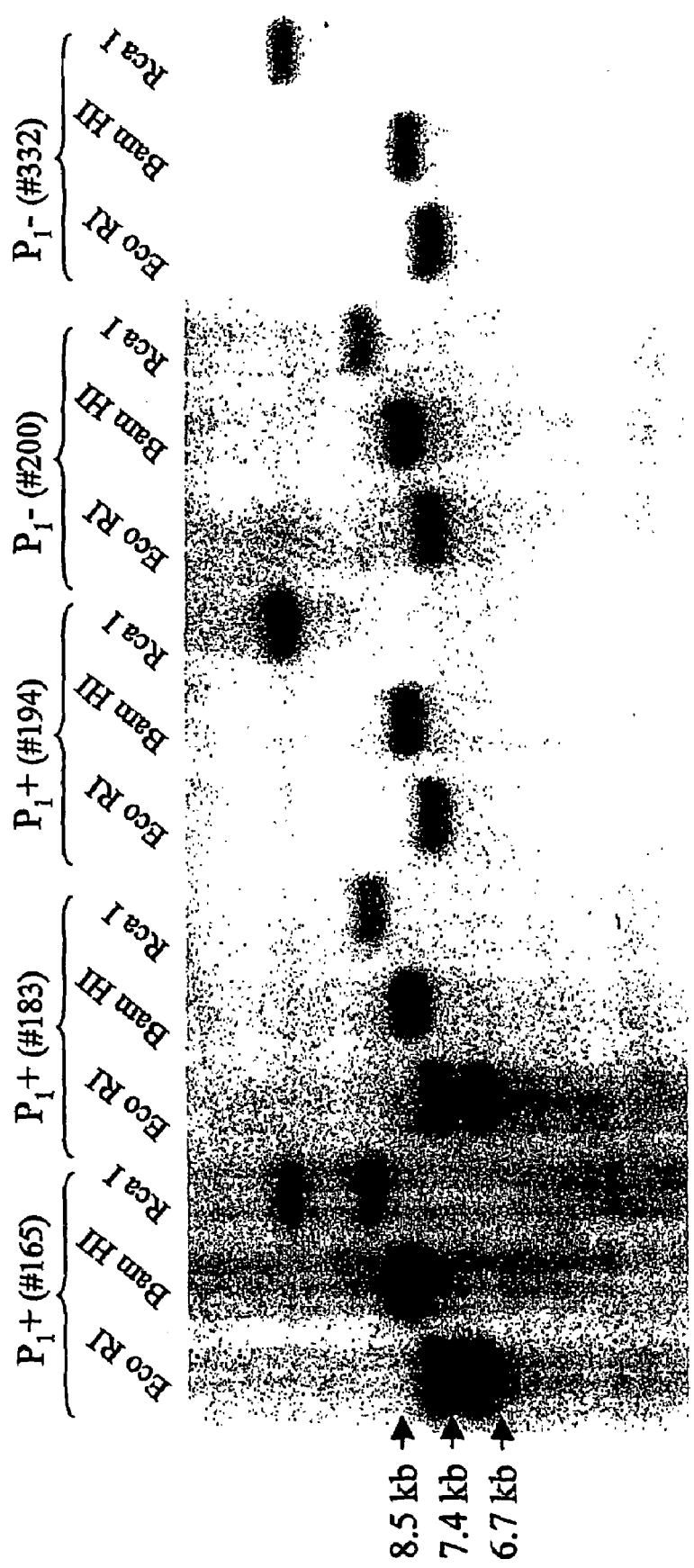
FIG. 3 is an illustration of RcaI genotyping of position A109G by Southern analysis. DNA from 5 phenotyped donors was digested with restriction enzymes as indicated, and the blot probed with the full coding α4Gal-T1 (#67) construct. The RcaI digestion confirmed the PCR based genotyping presented in Table II. The EcoRI polymorphism found in individuals #165 and #183 is outside the coding region of α4Gal-T1 and is unrelated to the $P_1$ phenotype.

All patent applications, patents, and literature references cited in this specification are hereby incorporated by reference in their entirety. In the case of conflict, the present description, including definitions, is intended to control.

Definitions

1. "Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases (see below).

2. "Complementary DNA or cDNA" as used herein refers to a DNA molecule or sequence that has been enzymatically synthesized from the sequences present in a mRNA template, or a clone of such a DNA molecule. A "DNA Construct" is a DNA molecule or a clone of such a molecule, either single- or double-stranded, which has been modified to contain segments of DNA that are combined and juxtaposed in a manner that would not otherwise exist in nature. By way of non-limiting example, a cDNA or DNA which has no introns is inserted adjacent to, or within, exogenous DNA sequences.

3. A plasmid or, more generally, a vector, is a DNA construct containing genetic information that may provide for its replication when inserted into a host cell. A plasmid generally contains at least one gene sequence to be expressed in the host cell, as well as sequences that facilitate such gene expression, including promoters and transcription initiation sites. It may be a linear or closed circular molecule.

4. Nucleic acids are "hybridizable" to each other when at least one strand of one nucleic acid can anneal to another nucleic acid under defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two nucleic acids contain substantially complementary sequences; depending on the stringency of hybridization, however, mismatches may be tolerated. Typically, hybridization of two sequences at high stringency (such as, for example, in an aqueous solution of 0.5×SSC, at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarity between the hybridizing sequences. (1×SSC is 0.15 M NaCl, 0.015 M Na citrate).

5. An "isolated" nucleic acid or polypeptide as used herein refers to a component that is removed from its original environment (for example, its natural environment if it is naturally occurring). An isolated nucleic acid or polypeptide contains less than about 50%, preferably less than about 75%, and most preferably less than about 90%, of the cellular components with which it was originally associated.

6. A "probe" refers to a nucleic acid that forms a hybrid structure with a sequence in a target region due to complementarily of at least one sequence in the probe with a sequence in the target region.

7. A nucleic acid that is "derived from" a designated sequence refers to a nucleic acid sequence that corresponds to a region of the designated sequence. This encompasses sequences that are homologous or complementary to the sequence, as well as "sequence-conservative variants" and "function-conservative variants". Sequence-conservative variants are those in which a change of one or more nucleotides in a given codon position results in no alteration in the amino acid encoded at that position. Function-conservative variants of α4Gal-T1 are those in which a given amino acid residue in the polypeptide has been changed without altering the overall conformation and enzymatic activity (including substrate specificity) of the native polypeptide; these changes include, but are not limited to, replacement of an amino acid with one having similar physico-chemical properties (such as, for example, acidic, basic, hydrophobic, and the like).

8. A "donor substrate" is a molecule recognized by, e.g., a α1,4galactosyltransferase and that contributes a galactose moiety for the transferase reaction. For α4Gal-T1, a donor substrate is UDP-galactose. An "acceptor substrate" is a molecule, preferably a saccharide or oligosaccharide, that is recognized by, e.g., a galactosyltransferase and that is the target for the modification catalyzed by the transferase, i.e., receives the galactose moiety. For α4Gal-T1, acceptor substrates include without limitation glycosphingolipids, oligosaccharides, glycoproteins, glycopeptides, and comprising the sequences Galβ1-4Glc, or Galβ1-3Glc.

9. In accordance with the present invention there may be employed conventional molecular biology, microbiology, and recombinant DNA techniques within the skill of the art. Such techniques are explained fully in the literature. See for example, Sambrook, Fritsch, Maniatis, Molecular Cloning: A Laboratory Manual, Second Edition (1989) Cold Spring Harbor Laboratory Press, Cold Spring Harbor, N.Y.); DNA Cloning: A Practical Approach, Volumes I and II (D. N. Glover ed. 1985); Oligonucleotide Synthesis (M. J. Gait ed. 1984); Nucleic Acid Hybridization B. D. Hames & S. J. Higgins eds. (1985); Transcription and Translation B. D. Hames & S. J. Higgins eds (1984); Animal Cell Culture R. I. Freshney, ed. (1986); Immobilized Cells and enzymes IRL Press, (1986); and B. Perbal, A Practical Guide to Molecular Cloning (1984).

10. The terms "sequence similarity" or "sequence identity" refer to the relationship between two or more amino acid or nucleic acid sequences, determined by comparing the sequences, which relationship is generally known as "homology". Identity in the art also means the degree of sequence relatedness between amino acid or nucleic acid sequences, as the case may be, as determined by the match between strings of such sequences. Both identity and similarity can be readily calculated (Computational Molecular Biology, Lesk, A. M., ed., Oxford University Press New York, 1988; Biocomputing: Informatics and Genome Projects, Smith, D. W. ed., Academic Press, New York, 1993; Computer Analysis of Sequence Data, Part I, Griffin, A. M., and Griffin, H. G. eds. Humana Press, New Jersey, 1994; Sequence Analysis in Molecular Biology, von Heinje, G., Academic Press, New York, 1987; and Sequence Analysis Primer, Gribskov, M. and Devereux, S., eds. M. Stockton Press, New York, 1991). While there are a number of existing methods to measure identity and similarity between two amino acid sequences or two nucleic acid sequences, both terms are well known to the skilled artisan (Sequence Analysis in Molecular Biology, von Hinge, G., Academic Press, New York, 1987; Sequence Analysis Primer, Gribskov, M. and Devereux, J., eds. M. Stockton Press, New York, 1991; and Carillo, H., and Lipman, D. SIAM J. Applied Math., 48.1073, 1988). Preferred methods for determining identity are designed to give the largest match between the sequences tested. Methods to determine identity are codified in computer programs. Preferred computer program methods for determining identity and similarity between two sequences include but are not limited to the GCG program package (20), BLASTP, BLASTN, and FASTA (21). Identity or similarity may also be determined using the alignment algorithm of Dayhoff et al. (Methods in Enzymology 91: 524-545 (1983)].

Preferably the nucleic acids of the present invention have substantial sequence identity using the preferred computer programs cited herein, for example greater than 40%, 45%, 50%, 60%, 70%, 75%, 80%, 85%, or 90% identity; more preferably at least 95%, 96%, 97%, 98%, or 99% sequence identity to the sequence shown in SEQ ID NO:1 or FIG. 1.

11. The polypeptides of the invention also include homologs of a α4Gal-T1 polypeptide and/or truncations thereof as described herein. Such homologs include polypeptides whose amino acid sequences are comprised of the amino acid sequences of α4Gal-T1 polypeptide regions from other species that hybridize under selected hybridization conditions (see discussion of hybridization conditions in particular stringent hybridization conditions herein) with a probe used to obtain a α4Gal-T1 polypeptide. These homologs will generally have the same regions which are characteristic of a α4Gal-T1 polypeptide. It is anticipated that a polypeptide comprising an amino acid sequence which has at least 40% identity or at least 60% similarity, preferably at least 60-65% identity or at least 80-85% similarity, more preferably at least 70-80% identity or at least 90-95% Similarity, most preferably at least 95% identity or at least 99% similarity with the amino acid sequence shown in SEQ. ID. NO. 2 or FIG. 1 or 2, will be a homolog of a α4Gal-T1 polypeptide. A percent amino acid sequence similarity or identity is calculated using the methods described herein, preferably the computer programs described herein.

Identification and Cloning of Human $P^k$ α4Gal-T1

A novel human α4GlcNAc-transferase gene responsible for the synthesis of the structures GlcNAcα1-4Galβ1-4GlcNAcβ1-R and GlcNAcα1-4Galβ1-3GalNacα1-R was reported (Nakayama et al., 1999). The gene was mapped to chromosome 3p14.3. Since this is the first mammalian glycosyltransferase gene available which forms an α1-4 linkage, we hypothesized that it could represent one member of a family of homologous glycosyltransferase genes. A characteristic feature of homologous glycosyltransferase genes is that different members may encode enzymes which have different donor or acceptor sugar specificities, but the nature of the linkage formed is often retained (Amado et al., 1999). BLAST analysis of databases using the coding region of the α4GlcNAc-transferase identified a sequenced BAC clone containing an open reading frame of 1059 bp with low sequence similarity. The identified gene here designated tentatively α4Gal-T1 had the coding region placed in a single exon. The coding region depicts a type II transmembrane protein of 353 amino acids with 35% overall sequence similarity to human α4GlcNAc-T (FIGS. 1 and 2). The two genes show conservation of a DxD motif (Wiggins and Munro, 1998), and spacings of five cysteine residues. The predicted coding region of α4Gal-T1 has a single initiation codon in agreement with Kozak's rule (Kozak, 1991), which precedes a sequence encoding a potential hydrophobic transmembrane segment (FIG. 1).

Genetic Polymorphism of $P^k$ α4Gal-T1

Sequence analysis of the α4Gal-T1 gene from six p phenotype individuals from northern Sweden revealed only one single homozygous missense mutation T548A leading to the change of residue 183 from methionine to lysine. This substitution is a few amino acid residues from the functionally important DxD motif (Wiggins and Munro, 1998). Although residue 183 is not invariant among α4Gal-T1 and the α4GlcNAc-T (M/I), the non-conservative substitution to a charged lysine residue may be expected to affect the function of the gene product. The finding that all six p individuals only revealed one missense homozygous mutation and this was not found in 12 $P_1$+/− individuals strongly indicated that the gene identified was the $P^k$ gene. Because α4Gal-T1 was located to the same chromosomal region (22q13.2) where the $P_1$ polymorphism has been linked (22q12-ter), it was likely that it also represented the $P_1$ synthase. Analysis of the α4Gal-T1 gene in $P_1$+ and $P_1$− individuals, revealed two silent and one missense mutation, however, none of these showed association with the P blood group phenotype (Table II).

TABLE II

Sequence polymorphisms identified in the coding region of α4Gal-T1 in $P_1$+, $P_1$−, and p blood group individuals.

| Donor number | Phenotype | nt. 109 Met$^{37}$-Val | nt. 548 Met$^{183}$-Lys | nt. 903 Silent Pro$^{301}$ | nt. 987 Silent Thr$^{329}$ |
|---|---|---|---|---|---|
| 165 | $P_1$+ | A/G | T | G | A/G |
| 167 | $P_1$+ | A/G | T | G | A/G |
| 178 | $P_1$+ | A/G | T | G | A/G |
| 183[a] | $P_1$+ | A | T | G/C | G |
| 168 | $P_1$+ | A | T | G/C | G |
| 173 | $P_1$+ | G | T | G | A |
| 194[a] | $P_1$+ | G | T | G | A |
| 332 | $P_1$− | G | T | G | A |
| 174 | $P_1$− | A | T | C | G |
| 200 | $P_1$− | A | T | C | G |
| 300[a] | $P_1$− | A | T | G/C | G |
| 321[a] | $P_1$− | G | T | G | A |
| 1 | p | A | A | G | A/G |
| 2 | p | A | A | G | G |
| 3 | p | A | A | G | G |
| 4 | p | A | A | G | G |
| 5 | p | A | A | G | G |
| 6 | p | A | A | G | G |

[a]Indicates that the sequence obtained by direct sequencing of PCR products were confirmed on cloned products.

This was confirmed by genotyping of 82 individuals, 31 $P_1$+ and 51 $P_1$−, where no significant correlation of the 109A and the 109G allele was observed (Table III).

TABLE III

Correlation of the missense polymorphism with
$P_1+/-$ blood group phenotype[a]

| Phenotype | Genotype nt. 109 | Cases | Allele frequencies | |
|---|---|---|---|---|
| | | | 109A | 109G |
| $P_1+$ | AA | 11 | 0.63 | 0.37 |
| | AG | 17 | | |
| | GG | 3 | | |
| $P_1-$ | AA | 32 | 0.79 | 0.21 |
| | AG | 17 | | |
| | GG | 2 | | |

[a]Genotyping was performed by RcaI restriction analysis of PCR products.

The PCR based RcaI restriction enzyme analysis was confirmed by Southern blot analysis of $P_1+/-$ individuals (FIG. 3). The more common allele of the missense mutation at A109G encodes a methionine at residue 37 in the C-terminal part of the putative hydrophobic signal sequence (FIG. 1). The conservative substitution of residue 37 to valine is not predicted to change the catalytic activity or affect retention in the Golgi.

The α4Gal-T1 gene characterized in this report provides a molecular genetic basis for the rare p histo-blood group phenotype found in Västerbotten County, northern part of Sweden (Cedergren, 1973). A single inactivating homozygous missense mutation in the catalytic domain of the enzyme was found in all six p phenotype individuals studied. We have previously characterized erythrocyte $PP^k$ antigen expression and α4Gal-T activity in EBV-transformed cells from two of these individuals (Wiels et al., 1996) and found a complete deficiency of $P^k$ antigen and α4Gal-T activity. Iizuka et al. (Iizuka et al., 1986) reporting essentially the same experiment suggested that a catalytically active $P^k$ transferase was indeed expressed in p individuals as evidenced by $P^k$ synthase activity in EBV-transformed cells; however, in accordance with the proposed p phenotype of the individual studied the transformed cells did not express $P^k$ antigen. This led Iizuka et al. (Iizuka et al., 1986) to suggest that p phenotype individuals carry a functionally active $P^k$ α4Gal-T gene, and that the p phenotype was a result of an yet unknown epigenetic mechanism. The data presented here are not in agreement with this, and support a simple allelic model with an active $P^k$ and an inactive p allele. It is, however, possible that the p phenotype in different populations has a different molecular genetic basis. The molecular genetics of all other characterized histo-blood group systems defined by carbohydrate antigens, i.e. ABO (Yamamoto et al., 1990), Hh (Kelly et al., 1994), Sese (Kelly et al., 1995), and Lewis (Mollicone et al., 1994; Nishihara et al., 1994), have been shown to adhere to a model with simple inactivating mutations of glycosyltransferase genes.

The presented data, however, do not explain the molecular genetic basis of the $P_1$ blood group polymorphism. Although the $P_1$ polymorphism is linked to the same chromosomal localization as α4Gal-T1, we found no genetic polymorphisms in the α4Gal-T1 gene associated with the $P_1+/-$ phenotypes, and recombinant α4Gal-T1 variants did not express $P_1$ synthase activity in vitro (Tables II and III, FIG. 4). Searching the available chromosome 22 sequence did not reveal additional homologous genes. Thus, essentially two possibilities exist: i) α4Gal-T1 can be activated by another non-homologous polymorphic gene or gene product and function as a $P_1$ synthase; or ii) a second polymorphic α4Gal-T gene, which is non-homologous to α4Gal-T1, exists. The former possibility has a precedent in two members of the β4Gal-T gene family, β4Gal-T1 and -T2, both of which are modulated by α-lactalbumin to change their, function from N-acetyllactosamine synthases to lactose synthases (Brodbeck et al., 1967; Brew et al., 1968; Almeida et al., 1997). Binding of α-Lactalbumin to these galactosyltransferases changes the acceptor substrate specificity from GlcNAc to Glc, but also to some degree affects the donor substrate specificity to include UDP-GalNAc (Do et al., 1995). The induction of β4Gal-T1 by α-lactalbumin to enable it to function as a lactose synthase is combined with a complex regulatory mechanism by which the β4Gal-T1 synthase is 100-fold upregulated in mammary glands (Charron et al., 1998). As lactose is the major nutrient in milk, this complex model for its synthesis appears to be in accordance with the biological function. The $P_1$ antigen has only been detected as a minor glycosphingolipid component, and no biological function for this polymorphic antigen has been identified. It therefore at present may seem less likely that a unique modulator of the α4Gal-T1 gene has evolved. The second possibility of the existence of another polymorphic non-homologous α4Gal-T gene located in the same chromosomal region implies that the encoded α4Gal-T functions as both $P^k$ and $P_1$ synthases. This is based on the findings that p individuals do not produce P1 antigens, and it is supported by the finding that erythrocytes of $P_1$ individuals contain relative less LacCer and more Gb3 than $P_2$ individuals (Fletcher et al., 1979). Generally, glycosyltransferases with similar functions are encoded by homologous glycosyltransferase gene families (Amado et al., 1999), however, recently two non-homologous β3GlcNAc-transferases both functioning as poly-N-acetyllactosamine synthases have been identified (Sasaki et al., 1997; Zhou et al., 1999).

α4Gal-T1 is homologous to an α4GlcNAc-T located at 3p14.3 (Nakayama et al., 1999). The (4GlcNAc-T forms the linkage GlcNAcα1-4Galβ1-3/4R, where R can be GalNAc, GlcNAc, or less effectively, glucose. Preference for mucin oligosaccharides of the core 2 structure was found, and the gene was shown to control expression of Con-A-binding class-III mucins in stomach and pancreas. Genetic polymorphisms in expression of the α4GlcNAc structures have not been reported. The sequence similarity with α4Gal-T1 (35% overall amino acid sequence similarity) is similar to that found among other homologous glycosyltransferases with similar functions, and the characteristic feature of conserved spacings of cysteine residues (five cysteine residues align, FIG. 2) is also found.

Both enzymes transfer to galactose, but while the acceptor disaccharide specificity of the α4GlcNAc-T appears to be broad, α4Gal-T1 is apparently highly specific for the glycolipid, lactosylceramide. Lopez et al. (Lopez et al., 1998) recently characterized an α4Gal-T activity in insect cells, and found it had preferred acceptor substrate specificity for Galβ1-3GalNAcα1-R rather than lacto-series structures. Thus, the acceptor substrate specificity is similar to that of the α4GlcNAc-T and different from α4Gal-T1.

Expression of $P^k$ α4Gal-T1 in Insect Cells

Figure 4:
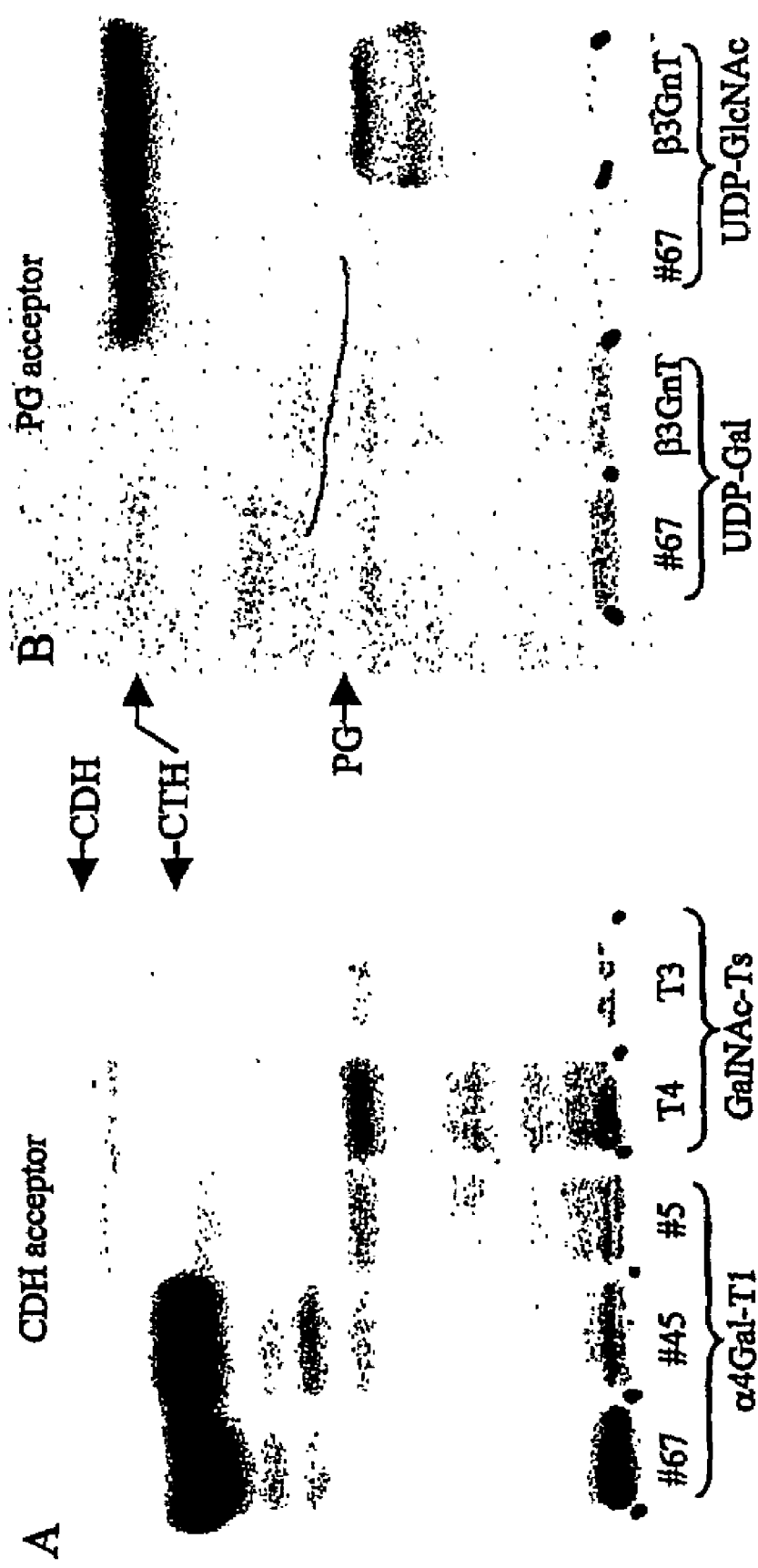
FIG. 4 illustrates expression of full coding Expression of full coding α4Gal-T1 variants in High Five cells. Assays were performed with microsomal fractions, and controls included constructs encoding polypeptide GalNAc-T3 and -T4 (Bennett et al., 1998), as well as a β3GlcNAc-T (Amado et al., 1999). Autoradiography of high performance thin-layer chromatography of reaction products (4 hr) purified by SepPack C-18 columns. Panel A: $P^k$ assay using 25 μg CDH as substrate. Plate was run in chloroform-methanol-water (60/35/8 v/v/v). Constructs from the two different alleles identified from $P_1$+/− individuals (#45 and #67) resulted in α4Gal-T activity toward CDH, while the construct derived from p (#5) showed no activity above background found with control constructs. Panel B: $P_1$ assay using 20 μg PG as substrate. Plate was run in chloroform-methanol-water (60/40/10 v/v/v). No specific product was formed with UDP-Gal donor substrate, whereas the β3GlcNAc-T transferred GlcNAc into PG with UDP-GlcNAc. Considerable GlcNAc-T activity was observed in both #67 and β3GnT microsomal fractions yielding a GlcNAc-CTH related product.

Expression of full coding constructs of α4Gal-T1$^{37M}$ and α4Gal-T1$^{37V}$ in insect cells resulted in marked increase in galactosyltransferase activity with CDH, compared to uninfected cells or cells infected with a control construct (FIG. 4). In contrast, no activity was found with the α4Gal-T1$^{183K}$ gene from p individuals. Importantly, neither α4Gal-T1$^{37M}$ or α4Gal-T1$^{37V}$ constructs conferred α4Gal-T activity with the neolacto-series (paragloboside) glycolipid acceptor for $P_1$ synthase activity (FIG. 4). The assay conditions for measuring $P^k$ and $P_1$ synthase activity was the same except substitution of the acceptor substrate, and these conditions were previously used to demonstrate both activities in kidney extracts from $P_1+$ and $P_1-$ individuals (Bailly et al., 1992). The soluble, secreted construct encoding residues 47-353 did not result in active α4Gal-T activity (data not shown). Attempts to obtain complete conversion of CDH to CTH were unsuccessful, but a 1-D $^1$H-NMR spectrum of the purified reaction mixture (not shown) clearly exhibited H-1 resonances diagnostic for CTH at levels approximately 30% of those of the CDH acceptor substrate. Thus, in addition to major resonances at 4.205 ppm ($^3J_{1,2}$=7.2 Hz) and 4.165 ppm ($^3J_{1,2}$=7.9 Hz), corresponding to H-1 of Galβ4 and Glcβ1of CDH, minor resonances were observed at 4.794 ppm ($^3J_{1,2}$=3.7 Hz) and 4.258 ppm ($^3J_{1,2}$=6.9 Hz), corresponding to H-1 of Galα4 and Galβ4 of CTH (the chemical shift of Glcβ1 H-1 is not affected by the addition of the terminal Galα4 residue). The chemical shift and $^3J_{1,2}$ coupling of the downfield H-1 resonance are particularly characteristic for Galα4 of CTH and other globo-series glycosphingolipids (Dabrowski et al., 1980; Kannagi et al., 1983). Analysis with a number of saccharide acceptors including lactose, lactosamine, and benzyl β-lacto-side, revealed no significant activity over background values.

Northern Analysis of α4Gal-T1

Figure 5:
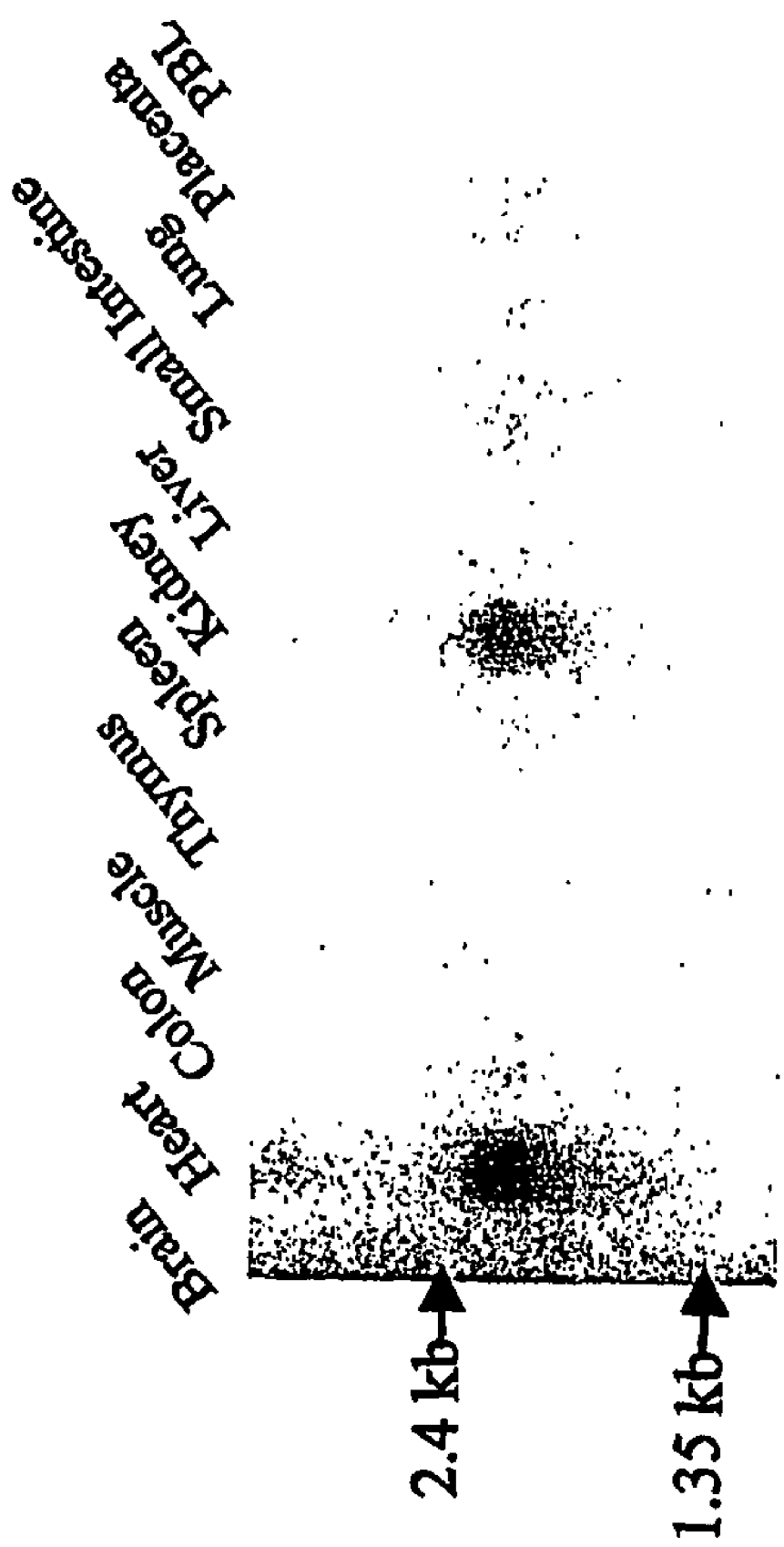
FIG. 5 is a photographic illustration of Northern blot analysis with human organs. Multiple human Northern blot (MTN-H12) was probed with $^{32}$P-labeled α4Gal-T1 probe.
Figure 6:
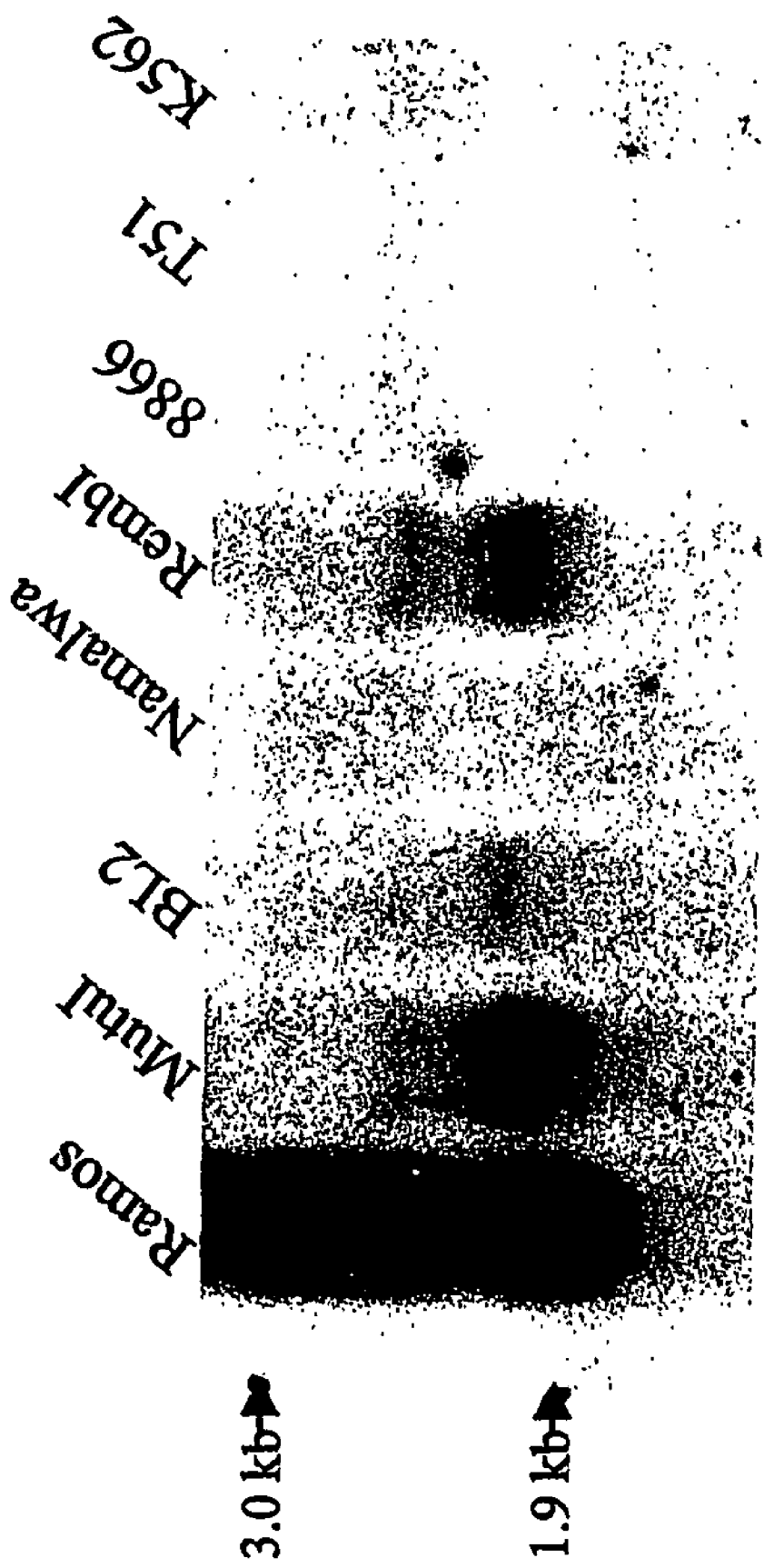
FIG. 6 is a photographic illustration of Northern blot analysis with eight human B cell lines. Transcript sizes are approximately 2 and 3 kb.
Figure 7:
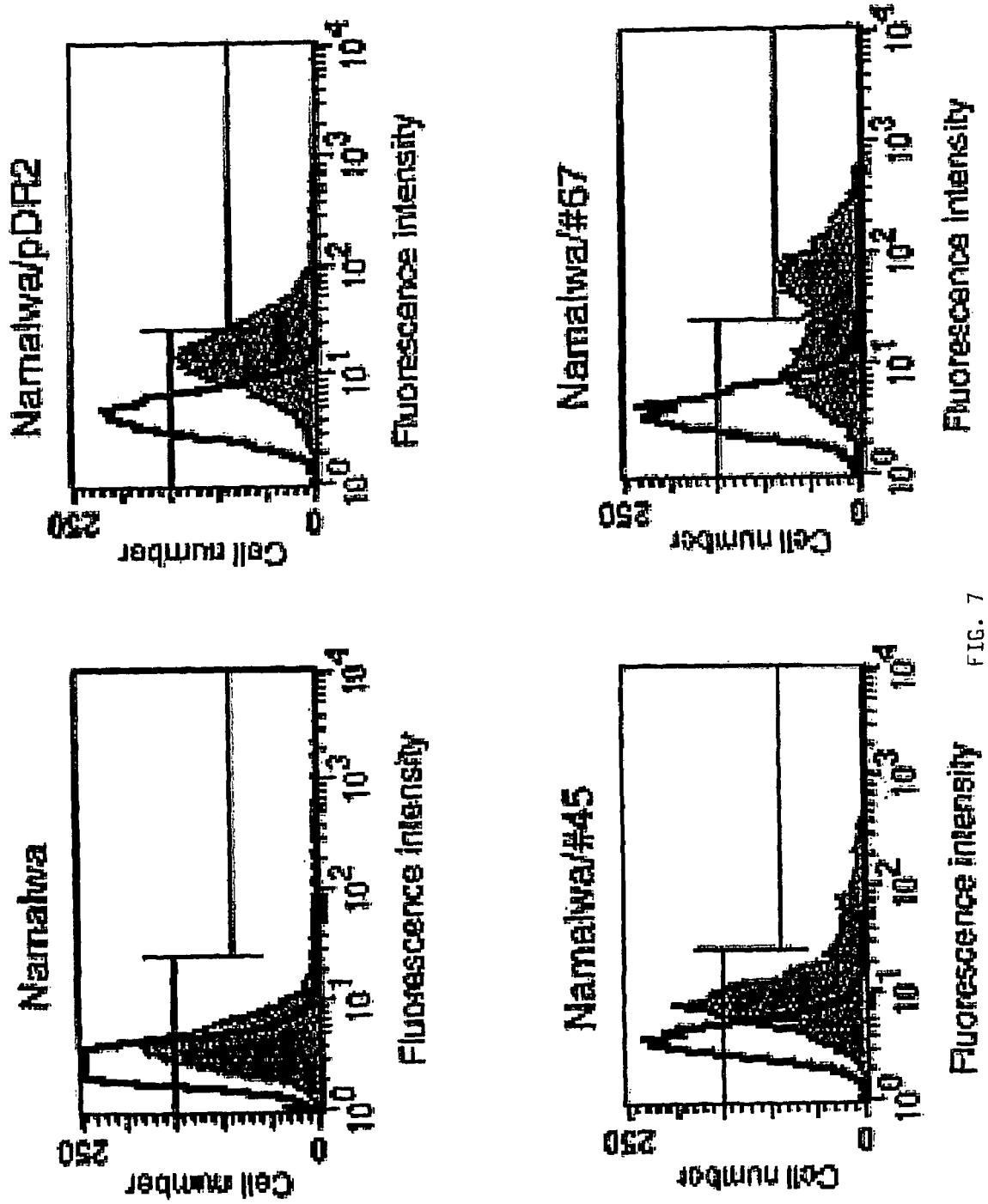
FIG. 7 illustrates cell surface expression of P$^k$/CD77 antigen in Namalwa cells after transient transfection of α4Gal-T1. Constructs p#5, #45, and #67, as well as empty pDR2 vector were electroporated in Namalwa cells and expression of P$^k$/CD77 antigen was tested after 48 hours. Cells were labeled with 1A4 monoclonal antibody and GAM-FITC (grey histograms) or with GAM-FITC alone (empty histograms) and analysed with a FACSCalibur flow cytometer.

Northern analysis with mRNA from 12 human organs revealed a ubiquitous expression pattern with high expression in kidney and heart and low expression in other organs (FIG. 5). The kidney primarily synthesizes globoseries glycosphingolipids (Clausen and Hakomori, 1989). Analysis of 8 human cell lines revealed an expression pattern correlating with α4Gal-T1 activity and cell surface expression of $P^k$ antigen (FIG. 6) (Taga et al., 1995b; Taga et al., 1995a). Ramos cells have the highest antigen expression and α4Gal-T activity, and strong expression of α4Gal-T1. In contrast, Namalwa cells that do not produce $P^k$ antigens and have no measurable α4Gal-T activity, showed no expression of α4Gal-T1. However, transient transfection of Namalwa cells with the full coding constructs of α4Gal-T1 (#67 and #45) clearly resulted in $P^k$/CD77 expression as revealed by FACS analysis (FIG. 7).

DNA, Vectors, and Host Cells

In practicing the present invention, many conventional techniques in molecular biology, microbiology, recombinant DNA, and immunology, are used. Such techniques are well known and are explained fully in, for example, Sambrook et al., 1989, *Molecular Cloning A Laboratory Manual*, Second Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984, (M. L. Gait ed.); *Nucleic Acid Hybridization*, 1985, (Hames and Higgins); *Transcription and Translation*, 1984 (Hames and Higgins eds.); *Animal Cell Culture*, 1986 (R. I. Freshney ed.); *Immobilized Cells and Enzymes*, 1986 (IRL Press); Perbal, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); *Methods in Enzymology* Vol. 154 and Vol. 155 (Wu and Grossman, and Wu, eds., respectively); *Immunochemical Methods in Cell and Molecular Biology*, 1987 (Mayer and Waler, eds; Academic Press, London); Scopes, 1987, *Protein Purification: Principles and Practice*, Second Edition (Springer-Verlag, N.Y.) and *Handbook of Experimental Immunology*, 1986, Volumes I-IV (Weir and Blackwell eds.).

The invention encompasses isolated nucleic acid fragments comprising all or part of the nucleic acid sequence disclosed herein as set forth in FIG. 1. The fragments are at least about 8 nucleotides in length, preferably at least about 12 nucleotides in length, and most preferably at least about 15-20 nucleotides in length. The invention further encompasses isolated nucleic acids comprising sequences that are hybridizable under stringency conditions of 2×SSC, 55° C., to the sequence set forth in FIG. 1; preferably, the nucleic acids are hybridizable at 2×SSC, 65° C.; and most preferably, are hybridizable at 0.5×SSC, 65° C.

The nucleic acids may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression.

The nucleic acids of the present invention may be flanked by natural human regulatory sequences, or may be associated with heterologous sequences, including promoters, enhancers, response elements, signal sequences, polyadenylation sequences, introns, 5'- and 3'-noncoding regions, and the like. The nucleic acids may also be modified by many means known in the art. Non-limiting examples of such modifications include methylation, "caps", substitution of one or more of the naturally occurring nucleotides with an analog, internucleotide modifications such as, for example, those with uncharged linkages (e.g., methyl phosphonates, phosphotriesters, phosphoroamidates, carbamates, etc.) and with charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

According to the present invention, useful probes comprise a probe sequence at least eight nucleotides in length that consists of all or part of the sequence from among the sequences as set forth in FIG. 1 or sequence-conservative or function-conservative variants thereof, or a complement thereof, and that has been labeled as described above.

The invention also provides nucleic acid vectors comprising the disclosed sequence or derivatives or fragments thereof. A large number of vectors, including plasmid and fungal vectors, have been described for replication and/or expression in a variety of eukaryotic and prokaryotic hosts, and may be used for gene therapy as well as for simple cloning or protein expression.

Recombinant cloning vectors will often include one or more replication systems for cloning or expression, one or more markers for selection in the host, e.g. antibiotic resistance, and one or more expression cassettes. The inserted coding sequences may be synthesized by standard methods, isolated from natural sources, or prepared as hybrids, etc. Ligation of the coding sequences to transcriptional regulatory elements and/or to other amino acid coding sequences may be achieved by known methods. Suitable host cells may be transformed/transfected/infected as appropriate by any suitable method including electroporation, CaCl$_2$ mediated DNA uptake, fungal infection, microinjection, microprojectile, or other established methods.

Appropirate host cells included bacteria, archaebacteria, fungi, especially yeast, and plant and animal cells, especially mammalian cells. Of particular interest are *Saccharomyces cerevisiae, Schizosaccharomyces pombe, Pichia pastoris, Hansenula polymorpha, Neurospora* spec., SF9 cells, C129 cells, 293 cells, and CHO cells, COS cells, HeLa cells, and immortalized mammalian myeloid and lymphoid cell lines. Preferred replication systems include M13, ColE1, 2μ, ARS, SV40, baculovirus, lambda, adenovirus, and the like. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced α4Gal-T1 derived peptides and polypeptides.

Advantageously, vectors may also include a transcription regulatory element (i.e., a promoter) operably linked to the α4Gal-T1 coding portion. The promoter may optionally contain operator portions and/or ribosome binding sites. Non-limiting examples of bacterial promoters compatible with *E. coli* include: β-lactamase (penicillinase) promoter; lactose promoter; tryptophan (trp) promoter; arabinose BAD operon promoter; lambda-derived P$_1$ promoters and N gene ribosome binding site; and the hybrid tac promoter derived from sequences of the trp and lac UV5 promoters. Non-limiting examples of yeast promoters include 3-phosphoglycerate kinase promoter, glyceraldehyde-3 phosphate dehydrogenase (GAPDH) promoter, galactokinase (GAL1) promoter, galactoepimerase (GAL10) promoter, metallothioneine (CUP) promoter and alcohol dehydrogenase (ADH) promoter. Suitable promoters for mammalian cells include without limitation viral promoters such as that from Simian Virus 40 (SV40), Rous sarcoma virus (RSV), adenovirus (ADV), and bovine papilloma virus (BPV). Mammalian cells may also require terminator sequences and poly A addition sequences and enhancer sequences which increase expression may also be included; sequences which cause amplification of the gene may also be desirable. Furthermore, sequences that facilitate secretion of the recombinant product from cells, including, but not limited to, bacteria, yeast, and animal cells, such as secretory signal sequences and/or prohormone pro region sequences, may also be included. These sequences are known in the art.

Nucleic acids encoding wild type or variant polypeptides may also be introduced into cells by recombination events. For example, such a sequence can be introduced into a cell, and thereby effect homologous recombination at the site of an endogenous gene or a sequence with substantial identity to the gene. Other recombination-based methods such as non-homologous recombinations or deletion of endogenous genes by homologous recombination may also be used.

The nucleic acids of the present invention find use, for example, as probes for the detection of α4Gal-T1 in other species or related organisms and as templates for the recombinant production of peptides or polypeptides. These and other embodiments of the present invention are described in more detail below.

Polypeptides and Antibodies

The present invention encompasses isolated peptides and polypeptides encoded by the disclosed cDNA sequence. Peptides are preferably at least five residues in length.

Nucleic acids comprising protein-coding sequences can be used to direct the recombinant expression of polypeptides in intact cells or in cell-free translation systems. The known genetic code, tailored if desired for more efficient expression in a given host organism, can be used to synthesize oligonucleotides encoding the desired amino acid sequences. The phosphoramidite solid support method of (26), the method of (27), or other well known methods can be used for such synthesis. The resulting oligonucleotides can be inserted into an appropriate vector and expressed in a compatible host organism.

The polypeptides of the present invention, including function-conservative variants of the disclosed sequence, may be isolated from native or from heterologous organisms or cells (including, but not limited to, bacteria, fungi, insect, plant, and mammalian cells) into which a protein-coding sequence has been introduced and expressed. Furthermore, the polypeptides may be part of recombinant fusion proteins.

Methods for polypeptide purification are well known in the art, including, without limitation, preparative discontiuous gel elctrophoresis, isoelectric focusing, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against a protein or against peptides derived therefrom can be used as purification reagents. Other purification methods are possible.

The present invention also encompasses derivatives and homologues of polypeptides. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

The present invention encompasses antibodies that specifically recognize immunogenic components derived from α4Gal-T1. Such antibodies can be used as reagents for detection and purification of α4Gal-T1.

α4Gal-T1 specific antibodies according to the present invention include polyclonal and monoclonal antibodies. The antibodies may be elicited in an animal host by immunization with α4Gal-T1 components or may be formed by in vitro immunization of immune cells. The immunogenic components used to elicit the antibodies may be isolated from human cells or produced in recombinant systems. The antibodies may also be produced in recombinant systems programmed with appropriate antibody-encoding DNA. with appropriate antibody-encoding DNA. Alternatively, the antibodies may be constructed by biochemical reconstitution of purified heavy and light chains. The antibodies include hybrid antibodies (i.e., containing two sets of heavy chain/light chain combinations, each of which recognizes a different antigen), chimeric antibodies (i.e., in which either the heavy chains, light chains, or both, are fusion proteins), and univalent antibodies (i.e., comprised of a heavy chain/light chain complex bound to the constant region of a second heavy chain). Also included are Fab fragments, including Fab' and F(ab)$_2$ fragments of antibodies. Methods for the production of all of the above types of antibodies and derivatives are well known in the art. For example, techniques for producing and processing polyclonal antisera are disclosed in Mayer and Walker, 1987, *Immunochemical Methods in Cell and Molecular Biology*, (Academic Press, London).

The antibodies of this invention can be purified by standard methods, including but not limited to preparative disc-gel elctrophoresis, isoelectric focusing, HPLC, reversed-phase HPLC, gel filtration, ion exchange and partition chromatography, and countercurrent distribution. Purification methods for antibodies are disclosed, e.g., in *The Art of Antibody Purification,* 1989, Amicon Division, W.R. Grace & Co. General protein purification methods are described in *Protein Purification: Principles and Practice*, R. K. Scopes, Ed., 1987, Springer-Verlag, New York, N.Y., U.S.A.

Anti α4Gal-T1 antibodies, whether unlabeled or labeled by standard methods, can be used as the basis for immunoassays. The particular label used will depend upon the type of immunoassay used. Examples of labels that can be used include, but are not limited to, radiolabels such as $^{32}$P, $^{125}$I, $^3$H and $^{14}$C; fluorescent labels such as fluorescein and its derivatives, rhodamine and its derivatives, dansyl and umbelliferone; chemiluminescers such as luciferia and 2,3-dihydrophthalazinediones; and enzymes such as horseradish peroxidase, alkaline phosphatase, lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well known in the art and are described in, e.g., Chan (Ed.), 1987, *Immunoassay: A Practical Guide*, Academic Press, Inc., Orlando, Fla.

Applications of the Nucleic Acid Moleclues, Polypeptides, and Antibodies of the Invention The nucleic acid molecules, α☐Gal-T1 polypeptide, and antibodies of the invention may be used in the prognostic and diagnostic evaluation of conditions associated with altered expression or activity of a polypeptide of the invention or conditions requiring modulation of a nucleic acid or polypeptide of the invention including proliferative disorders (e.g. cancer) and microbial infections (e.g. recurrent bladder infections), and the identification of subjects with a predisposition to such conditions (See below). Methods for detecting nucleic acid molecules and polypeptides of the invention can be used to monitor such conditions by detecting and localizing the polypeptides and nucleic acids. It would also be apparent to one skilled in the art that the methods described herein may be used to study the developmental expression of the polypeptides of the invention and, accordingly, will provide further insight into the role of the polypeptides. The applications of the present invention also include methods for the identification of substances or compounds that modulate the biological activity of a polypeptide of the invention (See below). The substances, compounds, antibodies etc., may be used for the treatment of conditions requiring modulation of polypeptides of the invention (See below).

Diagnostic Methods

A variety of methods can be employed for the diagnostic and prognostic evaluation of conditions requiring modulation of a nucleic acid or polypeptide of the invention, and the identification of subjects with a predisposition to such conditions. Such methods may, for example, utilize nucleic acids of the invention, and fragments thereof, and antibodies directed against polypeptides of the invention, including peptide fragments. In particular, the nucleic acids and antibodies may be used, for example, for: (1) the detection of the presence of α4Gal-T1 mutations, or the detection of either over- or under-expression of α4Gal-T1 mRNA relative to a non-disorder state or the qualitative or quantitative detection of alternatively spliced forms of α4Gal-T1 transcripts which may correlate with certain conditions or susceptibility toward such conditions; or (2) the detection of either an over- or an under-abundance of a polypeptide of the invention relative to a non-disorder state or the presence of a modified (e.g., less than full length) polypeptide of the invention which correlates with a disorder state, or a progression toward a disorder state.

The methods described herein may be performed by utilizing pre-packaged diagnostic kits comprising at least one specific nucleic acid or antibody described herein, which may be conveniently used, e.g., in clinical settings, to screen and diagnose patients and to screen and identify those individuals exhibiting a predisposition to developing a disorder.

Nucleic acid-based detection techniques and peptide detection techniques are described below. The samples that may be analyzed using the methods of the invention include those that are known or suspected to express α4Gal-T1 nucleic acids or contain a polypeptide of the invention. The methods may be performed on biological samples including but not limited to cells, lysates of cells which have been incubated in cell culture, chromosomes isolated from a cell (e.g. a spread of metaphase chromosomes), genomic DNA (in solutions or bound to a solid support such as for Southern analysis), RNA (in solution or bound to a solid support such as for northern analysis), cDNA (in solution or bound to a solid support), an extract from cells or a tissue, and biological fluids such as serum, urine, blood, and CSF. The samples may be derived from a patient or a culture.

Methods for Detection Nucleic Acid Molecules of the Invention

The nucleic acid molecules of the invention allow those skilled in the art to construct nucleotide probes for use in the detection of nucleic acid sequences of the invention in biological materials. Suitable probes include nucleic acid molecules based on nucleic acid sequences encoding at least 5 sequential amino acids from regions of the α4Gal-T1 polypeptide (see SEQ. ID. No. 10), preferably they comprise 15 to 50 nucleotides, more preferably 15 to 40 nucleotides, most preferably 15-30 nucleotides. A nucleotide probe may be labeled with a detectable substance such as a radioactive label that provides for an adequate signal and has sufficient half-life such as $^{32}$P, $^3$H, $^{14}$C or the like. Other detectable substances that may, be used include antigens that are recognized by a specific labeled antibody, fluorescent compounds, enzymes, antibodies specific for a labeled antigen, and luminescent compounds. An appropriate label may be selected having regard to the rate of hybridization and binding of the probe to the nucleotide to be detected and the amount of nucleotide available for hybridization. Labeled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect α4Gal-T1 genes, preferably in human cells. The nucleotide probes may also be used for example in the diagnosis or prognosis of conditions such as cancer and infections, and in monitoring the progression of these conditions, or monitoring a therapeutic treatment.

The probe may be used in hybridisation techniques to detect a α4Gal-T1 gene. The technique generally involves contacting and incubating nucleic acids (e.g. recombinant DNA molecules, cloned genes) obtained from a sample from a patient or other cellular source with a probe of the present invention under conditions favourable for the specific annealing of the probes to complementary sequences in the nucleic acids. Alter incubation, the non-annealed nucleic acids are removed, and the presence of nucleic acids that have hybridized to the probe if any are detected.

The detection of nucleic acid molecules of the invention may involve the amplification of specific gene sequences using an amplification method (e.g. PCR), followed by the analysis of the amplified molecules using techniques known to those skilled in the art. Suitable primers can be routinely designed by one of skill in the art. For example, primers may be designed using commercially available software, such as OLIGO 4.06 Primer Analysis software (National Biosciences, Plymouth, Minn.) or another appropriate program, to be about 22 to 30 nucleotides in length, to have a GC content of about 50% or more, and to anneal to the template at temperatures of about 60° C. to 72° C.

Genomic DNA may be used in hybridization or amplification assays of biological samples to detect abnormalities involving α4Gal-T1 nucleic acid structure, including point mutations, insertions, deletions, and chromosomal rearrangements. For example, direct sequencing, single stranded conformational polymorphism analyses, heteroduplex analysis, denaturing gradient gel electrophoresis, chemical mismatch cleavage, and oligonucleotide hybridization may be utilized.

Genotyping techniques known to one skilled in the art can be used to type polymorphisms that are in close proximity to the mutations in a α4Gal-T1 gene. The polymorphisms may be used to identify individuals in families that are likely to carry mutations. If a polymorphism exhibits linkage disequalibrium with mutations in the G2GnT3 gene, it can also be used to screen for individuals in the general population likely to carry mutations. Polymorphisms which may be used include restriction fragment length polymorphisms (RFLPs), single-nucleotide polymorphisms (SNP), and simple sequence repeat polymorphisms (SSLPs).

A probe or primer of the invention may be used to directly identify RFLPs. A probe or primer of the invention can additionally be used to isolate genomic clones such as YACs, BACs, PACs, cosmids, phage or plasmids. The DNA in the clones can be screened for SSLPs using hybridization or sequencing procedures.

Hybridization and amplification techniques described herein may be used to assay qualitative and quantitative aspects of α4Gal-T1 expression. For example RNA may be isolated from a cell type or tissue known to express α4Gal-T1 and tested utilizing the hybridization (e.g. standard Northern analyses) or PCR techniques referred to herein. The techniques may be used to detect differences in transcript size that may be doe to normal or abnormal alternative splicing. The techniques may be used to detect quantitative differences between levels of full length and/or alternatively splice transcripts detected in normal individuals relative to those individuals exhibiting symptoms of a disease.

The primers and probes may be used in the above described methods in situ i.e directly on tissue sections (fixed and/or frozen) of patient tissue obtained from biopsies or resections.

Oligonucleotides or longer fragments derived from any of the nucleic acid molecules of the invention may be used as targets in a microarray. The microarray can be used to simultaneously monitor the expression levels of large numbers of genes and to identify genetic variants, mutations, and polymorphisms. The information from the microarray may be used to determine gene function, to understand the genetic basis of a disorder, to identify predisposition to a disorder, to treat a disorder, to diagnose a disorder, and to develop and monitor the activities of therapeutic agents.

The preparation, use, and analysis of micro arrays are well known to a person skilled in the art. (See, for example, Brennan, T. M. et al. (1995) U.S. Pat. No. 5,474,796; Schena, et al. (1996) Proc. Natl. Acad. Sci. 93:10614-10619; Baldeschweiler et al. (1995), PCT Application WO95/251116; Shalon, D. et al. (1995) PCT application WO95/35505; Heller, R. A. et al. (1997) Proc. Natl. Acad. Sci. 94:2150-2155; and Heller, M. J. et al. (1997) U.S. Pat. No. 5,605,662.)

Methods for Detecting Polypeptides

Antibodies specifically reactive with a α4Gal-T1 Polypeptide, or derivatives, such as enzyme conjugates or labeled derivatives, may be used to detect α4Gal-T1 polypeptides in various biological materials. They may be used as diagnostic or prognostic reagents and they may be used to detect abnormalities in the level of α4Gal-T1 polypeptides, expression, or abnormalities in the structure, and/or temporal, tissue, cellular, or subcellular location of the polypeptides. Antibodies may also be used to screen potentially therapeutic compounds in vitro to determine their effects on a condition such as cancer or microbial infections. In vitro immunoassays may also be used to assess or monitor the efficacy of particular therapies.

The antibodies of the invention may also be used in vitro to determine the level of α4Gal-T1 polypeptide expression in cells genetically engineered to produce a α4Gal-T1 polypeptide. The antibodies may be used to detect and quantify polypeptides of the invention in a sample in order to determine their role in particular cellular events or pathological states, and to diagnose and treat such pathological states.

In particular, the antibodies of the invention may be used in immuno-histochemical analyses, for example, at the cellular and sub-subcellular level, to detect a polypeptide of the invention, to localize it to particular cells and tissues, and to specific subcellular locations, and to quantitate the level of expression.

The antibodies may be used in any known immunoassays that rely on the binding interactions between an antigenic determinant of a polypeptide of the invention, and the antibodies. Examples of such assays are radio immunoassays, enzyme immunoassays (e.g. ELISA), immunofluorescence, immunoprecipitation, latex agglutination, hemagglutination, and histochemical tests.

Cytochemical techniques known in the art for localizing antigens using light and electron microscopy may be used to detect a polypeptide of the invention. Generally, an antibody of the invention may be labeled with a detectable substance and a polypeptide may be localised in tissues and cells based upon the presence of the detectable substance. Various methods of labeling polypeptides are known in the art and may be used. Examples of detectable substances include, but are not limited to, the following: radioisotopes (e.g., $^3$H, $^{14}$C, $^{35}$S $^{125}$I, $^{131}$I), fluorescent labels (e.g., FITC, Rhodamine, lanthanide phosphors), luminescent labels such as luminol, enzymatic labels (e.g., horseradish peroxidase, β-galactosidase, luciferase, alkaline phosphatase, acetylcholinesterase), biotinyl groups (which can be detected by marked avidin e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). In some embodiments, labels are attached via spacer arms of various lengths to reduce potential steric hindrance. Antibodies may also be coupled to electron dense substances, such as ferritin or colloidal gold, which are readily visualised by electron microscopy.

The antibody or sample may be immobilized on a carrier or solid support which is capable of immobilizing cells, antibodies, etc. For example, the carrier or support may be nitrocellulose, or glass, polyacrylamides, gabbros, and magnetite. The support material may have any possible configuration including spherical (e.g. bead), cylindrical (e.g. inside surface of a test tube or well, or the external surface of a rod), or flat (e.g. sheet, test strip). Indirect methods may also be employed in which the primary antigen-antibody reaction is amplified by the introduction of a second antibody, having specificity for the antibody reactive against a polypeptide of the invention. By way of example, if the antibody having specificity against a polypeptide of the invention is a rabbit IgG antibody, the second antibody may be goat anti-rabbit gamma-globulin labeled with a detectable substance as described herein.

Where a radioactive label is used as a detectable substance, a polypeptide of the invention may be localized by radioautography. The results of radioautography may be quantitated by determining the density of particles in the radioautographs by various optical methods, or by counting the grains.

A polypeptide of the invention may also be detected by assaying for α4Gal-T1 activity as described herein. For example, a sample may be reacted with an acceptor substrate and a donor substrate under conditions where a α4Gal-T1 polypeptide is capable of transferring the donor substrate to the acceptor substrate to produce a donor substrate-acceptor substrate complex.

Methods for Identifying or Evaluating Substances/Compounds

The methods described herein are designed to identify substances and compounds that modulate the expression or biological activity of a α4Gal-T1 polypeptide including substances that interfere with or enhance the expression or activity of a α4Gal-T1 polypeptide.

Substances and compounds identified using the methods of the invention include but are not limited to peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies [e.g. polyclonal, monoclonal, humanized, anti-idiotypic, chimeric, single chain antibodies, fragments, (e.g. Fab, F(ab)$_2$, and Fab expression library fragments, and epitope-binding fragments thereof)], polypeptides, nucleic acids, carbohydrates, and small organic or inorganic molecules. A substance or compound may be an endogenous physiological compound or it may be a natural or synthetic compound.

Substances which modulate a α4Gal-T1 polypeptide can be identified based on their ability to associate with a α4Gal-T1 polypeptide. Therefore, the invention also provides methods for identifying substances that associate with a α4Gal-T1 polypeptide. Substances identified using the methods of the invention may be isolated, cloned and sequenced using conventional techniques. A substance that associates with a polypeptide of the invention may be an agonist or antagonist of the biological or immunological activity of a polypeptide of the invention. The term "agonist" refers to a molecule that increases the amount of, or prolongs the duration of, the activity of the polypeptide. The term "antagonist" refers to a molecule which decreases the biological or immunological activity of the polypeptide. Agonists and antagonists may include proteins, nucleic acids, carbohydrates, or any other molecules that associate with a polypeptide of the invention.

Substances which can associate with a α4Gal-T1 polypeptide may be identified by reacting a α4Gal-T1 polypeptide with a test substance which potentially associates with a α4Gal-T1 polypeptide, under conditions which permit the association, and removing and/or detecting the associated α4Gal-T1 polypeptide and substance. The substance-polypeptide complexes, free substance, or non-complexed polypeptides may be assayed. Conditions which permit the formation of substance-polypeptide complexes may be selected having regard to factors such as the nature and amounts of the substance and the polypeptide.

The substance-polypeptide complex, free substance or non-complexed polypeptides may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against a polypeptide of the invention or the substance, or labeled polypeptide, or a labeled substance may be utilized. The antibodies, polypeptides, or substances may be labeled with a detectable substance as described above.

A α4Gal-T1 polypeptide, or the substance used in the method of the invention may be insolubilized. For example, a polypeptide, or substance may be bound to a suitable carrier such as agarose, cellulose, dextran, "Sephadex®", "Sepharose®", carboxymethyl cellulose, polystyrene, filter paper, ion-exchange resin, plastic film, plastic tube, glass beads, polyamine-methyl vinyl-ether-maleic acid copolymer, amino acid copolymer, ethyl-ene-maleic acid copolymer, nylon, silk, etc. The carrier may be in the shape of, for example, a tube, test plate, beads, disc, sphere etc. The insolubilized polypeptide or substance may be prepared by reacting the material with a suitable insoluble carrier using known chemical or physical methods, for example, cyanogen bromide coupling.

The invention also contemplates a method for evaluating a compound for its ability to modulate the biological activity of a polypeptide of the invention, by assaying for an agonist or antagonist (i.e. enhancer or inhibitor) of the association of the polypeptide with a substance that interacts with the polypeptide (e.g. donor or acceptor substrates or parts thereof). The basic method for evaluating if a compound is an agonist or antagonist of the association of a polypeptide of the invention and a substance that associates with the polypeptide is to prepare a reaction mixture containing the polypeptide and the substance under conditions which permit the formation of substance-polypeptide complexes, in the presence of a test compound. The test compound may be initially added to the mixture, or may be added subsequent to the addition of the polypeptide and substance. Control reaction mixtures without the test compound or with a placebo are also prepared. The formation of complexes is detected and the formation of complexes in the control reaction but not in the reaction mixture indicates that the test compound interferes with the interaction of the polypeptide and substance. The reactions may be carried out in the liquid phase or the polypeptide, substance, or test compound may be immobilized as described herein.

It will be understood that the agonists and antagonists i.e. inhibitors and enhancers, that can be assayed using the methods of the invention may act on one or more of the interaction sites an the polypeptide or substance including agonist binding sites, competitive antagonist binding cites, non-competitive antagonist binding sites or allosteric sites.

The invention also makes it possible to screen for antagonists that inhibit the effects of an agonist of the interaction of a polypeptide of the invention with a substance which is capable of associating with the polypeptide. Thus, the invention may be used to assay for a compound that competes for the same interacting site of a polypeptide of the invention.

Substances that modulate a α4Gal-T1 polypeptide of the invention can be identified based on their ability to interfere with or enhance the activity of a α4Gal-T1 polypeptide. Therefore, the invention provides a method for evaluating a compound for its ability to modulate the activity of a α4Gal-T1 polypeptide comprising (a) reacting an acceptor substrate and a donor substrate for a α4Gal-T1 polypeptide in the presence of a test substance; (b) measuring the amount of donor substrate transferred to acceptor substrate, and (c) carrying out steps (a) and (b) in the absence of the test substance to determine if the substance interferes with or enhances transfer of the sugar donor to the acceptor by the α4Gal-T1 polypeptide.

Suitable acceptor substrate for use in the methods of the invention are a saccharide, oligosaccharides, polysaccharides, polypeptides, glycopolypeptides, or glycolipids which are either synthetic with linkers at the reducing end or naturally occuring structures, for example, asialo-agalacto-fetuin glycopeptide. Acceptors will generally comprise a β-D-galactosyl-1,4-D-glucosyl linkage.

The donor substrate may be a nucleotide sugar, dolichol-phosphate-sugar or dolichol-pyrophosphate-oligosaccharide, for example, uridine diphospho-galactose (UDP-Gal), or derivatives or analogs thereof. The α4Gal-T1 polypeptide may be obtained from natural sources or produced used recombinant methods as described herein.

The acceptor or donor substrates may be labeled with a detectable substance as described herein, and the interaction of the polypeptide of the invention with the acceptor and donor will give rise to a detectable change. The detectable change may be calorimetric, photometric, radiometric, potentiometric, etc. The activity of α4Gal-T1 polypeptide of the invention may also be determined using methods based on HPLC (Koenderman et al., FEBS Lett. 222:42, 1987) or methods employed synthetic oligosaccharide acceptors attached to hydrophobic aglycones (Palcic et al Glycoconjugate 5:49, 1988; and Pierce et al, Biochem. Biophys. Res. Comm. 146: 679, 1987).

The α4Gal-T1 polypeptide is reacted with the acceptor and donor substrates at a pH and temperature effective for the polypeptide to transfer the donor to the acceptor, and where one of the components is labeled, to produce a detectable change. It is preferred to use a buffer with the acceptor and donor to maintain the pH within the pH range effective for the polypeptides. The buffer, acceptor and donor may be used as an assay composition. Other compounds such as EDTA and detergents may be added to the assay composition.

The reagents suitable for applying the methods of the invention to evaluate compounds that modulate a α4Gal-T1 polypeptide may be packaged into convenient kits providing the necessary materials packaged into suitable containers. The kits may also include suitable supports useful in performing the methods of the invention.

Substances that modulate a α4Gal-T1 polypeptide can also be identified by treating immortalized cells which express the polypeptide with a test substance, and comparing the morphology of the cells with the morphology of the cells in the absence of the substance and/or with immortalized cells which do not express the polypeptide. Examples of immortalized cells that can be used include lung epithelial cell lines such as MvlLu or HEK293 (human embryonal kidney) transfected with a vector containing a nucleic acid of the invention. In the absence of an inhibitor the cells show signs of morphologic transformation (e.g. fibroblastic morphology, spindle shape and pile up; the cells are less adhesive to substratum; there is less cell to cell contact in monolayer culture; there is reduced growth-factor requirements for survival and proliferation; the cells grow in soft-agar of other semi-solid medium; there is a lack of contact inhibition and increased apoptosis in low-serum high density cultures; there is enhanced cell motility, and there is invasion into extracellular matrix and secretion of proteases). Substances that inhibit one or more phenotypes may be considered an inhibitor.

A substance that inhibits a α4Gal-T1 polypeptide may be identified by treating a cell which expresses the polypeptide with a test substance, and assaying for globoseries structures (e.g. $P^k$, P, Gal-globoside, sialosyl-Gal-globoside, or fucosyl-Gal-globoside) associated with the cell. The globoseries structures can be assayed using a substance that binds to the structures (e.g. antibodies). Cells that have not been treated with the substance or which do not express the polypeptide may be employed as controls.

Substances which inhibit transcription or translation of a α4Gal-T1 gene may be identified by transfecting a cell with an expression vector comprising a recombinant molecule of the invention, including a reporter gene, in the presence of a test substance and comparing the level of expression of the α4Gal-T1 polypeptide, or the expression of the polypeptide encoded by the reporter gene with a control cell transfected with the nucleic acid molecule in the absence of the substance. The method can be used to identify transcription and translation inhibitors of a α4Gal-T1 gene.

Compositions and Treatments

The substances or compounds identified by the methods described herein, polypeptides, nucleic acid molecules, and antibodies of the invention may be used for modulating the biological activity of a α4Gal-T1 polypeptide, and they may be used in the treatment of conditions mediated by a α4Gal-T1 polypeptide. In particular, they may be used to combat cancers, e.g. Burkits lymphoma and microbial infections, and they may be used in the prevention and treatment of bacterial infections.

Therefore, the present invention may be useful for diagnosis or treatment of various neoplastic and infectious disorders in mammals, preferably humans. Such disorders include the following: tumors and cancers, bacterial infections, effects of toxins, viral infections, and the like.

The substances or compounds identified by the methods described herein, antibodies, and polypeptides, and nucleic acid molecules of the invention may be useful in the prevention and treatment of tumors. The substances etc. are particularly useful in the prevention and treatment of microbial pathogens and the adhesion of such to mucosal surfaces.

A substance or compound identified in accordance with the methods described herein, antibodies, polypeptides, or nucleic acid molecules of the invention may be used to modulate expression of receptors for bacteria, toxins, vira etc, and/or confer protection against such pathogens in a subject.

Accordingly, the substances, antibodies, and compounds may be formulated into pharmaceutical compositions for administration to subjects in a biologically compatible form suitable for administration in vivo. By biologically compatible form suitable for administration in vivo is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response. For example, several divided doses may be administeted daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions that may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances or compounds in association with one or more pharmaceutically acceptable vehicles or diluents, and contained in buffered solutions with a suitable pH and iso-osmotic with the physiological fluids.

After pharmaceutical compositions have been prepared, they can be placed in an appropriate container and labeled for treatment of an indicated condition. For administration of an inhibitor of a polypeptide of the invention, such labeling would include amount, frequency, and method of administration.

The nucleic acids encoding α4Gal-T1 polypeptides or any fragment thereof, or antisense sequences may be used for therapeutic purposes. Antisense to a nucleic acid molecule encoding a polypeptide of the invention may be med in situations to block the synthesis of the polypeptide. In particular, cells may be transformed with sequences complementary to nucleic acid molecules encoding α4Gal-T1 polypeptide. Thus, antisense sequences may be used to modulate α4Gal-T1 activity or to achieve regulation of gene function. Sense or antisense oligomers or larger fragments, can be designed from various locations along the coding or regulatory regions of sequences encoding a polypeptide of the invention.

Expression vectors may be derived from retroviruses, adenoviruses, herpes or vaccinia viruses or from various bacterial plasmids for delivery of nucleic acid sequences to the target organ, tissue, or cells. Vectors that express antisense nucleic acid sequences of α4Gal-T1 polypeptide can be constructed using techniques well known to those skilled in the art (see for example, Sambrook, Fritsch, Maniatis, Molecular Cloning, A Laboratory Manual, Second Edition (1989) Cold Spring Harbor Laboratory Press, Cold Spring Harbor, N.Y.).

Genes encoding α4Gal-T1 polypeptide can be turned off by transforming a cell or tissue with expression vectors that express high levels of a nucleic acid molecule or fragment thereof which encodes a polypeptide of the invention. Such constructs may be used to introduce untranslatable sense or antisense sequences into a cell. Even if they do not integrate into the DNA, the vectors may continue to transcribe RNA molecules until all copies are disabled by endogenous nucleases. Transient expression may last for extended periods of time (e.g. a month or more) with a non-replicating vector or if appropriate replication elements are part of the vector system.

Modification of gene expression may be achieved by designing antisense molecules, DNA, RNA, or PNA, to the control regions of a α4Gal-T1 polypeptide gene i.e. the promoters, enhancers, and introns. Preferably the antisense molecules are oligonucleotides derived from the transcription initiation site (e.g. between positions −10 and +10 from the start site). Inhibition can also be achieved by using triple-helix base-pairing techniques. Triple helix pairing causes inhibition of the ability of the double helix to open sufficiently for the binding of polymerases, transcription factors, or regulatory molecules (see Gee J. E. et al (1994) In: Huber, B. E. and B. I. Carr, Molecular and Immunologic Approaches, Futura Publishing Co., Mt. Kisco, N.Y.).

Ribozymes, enzymatic RNA molecules, may be used to catalyze the specific cleavage of RNA. Ribozyme action involves sequence-specific hybridization of the ribozyme molecule to complementary target RNA, followed by endonucleolytic cleavage. For example, hammerhead motif ribozyme molecules may be engineered that can specifically and efficiently catalyze endonucleolytic cleavage of sequences encoding a polypeptide of the invention.

Specific ribosome cleavage sites within any RNA target may be initially identified by scanning the target molecule for ribozyme cleavage sites which include the following sequences: GUA, GUU, and GUC. Short RNA sequences of between 15 and 20 ribonucleotides corresponding to the region of the cleavage site of the target gene may be evaluated for secondary structural features which may render the oligonucleotide inoperable. The suitability of candidate targets may be evaluated by testing accessibility to hybridization with complementary oligonucleotides using ribonuclease protection assays.

Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The therapeutic index is the dose ratio of therapeutic to toxic effects and it can be expressed as the $ED_{50}/LD_{50}$ ratio. Pharmaceutical compositions which exhibit large therapeutic indices are preferred.

The invention also provides methods for studying the function of a α4Gal-T1 polypeptide. Cells, tissues, and non-human animals lacking in α4Gal-T1 expression or partially lacking in α4Gal-T1 expression may be developed using recombinant expression vectors of the invention having specific deletion or insertion mutations in a α4Gal-T1 gene. A recombinant expression vector may be used to inactivate or alter the endogenous gene by homologous recombination, and thereby create a α4Gal-T1 deficient cell, tissue or animal.

Null alleles may be generated in cells, such as embryonic stem cells by deletion mutation. A recombinant α4Gal-T1 gene may also be engineered to contain an insertion mutation which inactivates α4Gal-T1. Such a construct may then be introduced into a cell, such as an embryonic stem cell, by a technique such as transfection, electroporation, injection etc. Cells lacking an intact α4Gal-T1 gene may then be identified, for example by Southern blotting, Northern Blotting or by assaying for expression of a polypeptide of the invention using the methods described herein. Such cells may then be used to generate transgenic non-human animals deficient in α4Gal-T1. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific cell populations, developmental patterns and in vivo processes, normally dependent on α4Gal-T1 expression.

The invention thus provides a transgenic non-human mammal all of whose germ cells and somatic cells contain a recombinant expression vector that inactivates or alters a gene encoding a α4Gal-T1 polypeptide. Further the invention provides a transgenic non-human mammal, which does not express a α4Gal-T1 polypeptide of the invention.

A transgenic non-human animal includes but is not limited to mouse, rat, rabbit, sheep, hamster, guinea pig, micro-pig, pig, dog, cat, goat, and non-human primate, preferably mouse.

The invention also provides a transgenic non-human animal assay system which provides a model system for testing for an agent that reduces or inhibits a pathology associated with a α4Gal-T1 polypeptide comprising: (a) administering the agent to a transgenic non-human animal of the invention; and (b) determining whether said agent reduces or inhibits the pathology in the transgenic non-human animal relative to a transgenic non-human animal of step (a) which has not been administered the agent.

The agent may be useful to treat the disorders and conditions discussed herein. The agents may also be incorporated in a pharmaceutical composition as described herein.

A polypeptide of the invention may be used to support the survival, growth, migration, and/or differentiation of cells expressing the polypeptide. Thus, a polypeptide of the invention may be used as a supplement to support, for example cells in culture.

Methods to Prepare Oligosaccharides

The invention relates to a method for preparing an oligosaccharide comprising contacting a reaction mixture comprising an activated donor substrate e.g. GlcNAc, and an acceptor substrate in the presence of a polypeptide of the invention.

Examples of acceptor substrates for use in the method for preparing an oligosaccharide are a saccharide, oligosaccharides, polysaccharides, glycopeptides, glycopolypeptides, or glycolipids which are either synthetic with linkers at the reducing end or naturally occurring structures, for example, asialo-agalacto-fetuin glycopeptide. The activated donor substrate is preferably GlcNAc which may be part of a nucleotide-sugar, a dolichol-phosphate-sugar, or dolichol-pyrophosphate-oligosaccharide.

In an embodiment of the invention, the oligosaccharides are prepared on a carrier that is non-toxic to a mammal, in particular a human such as a lipid isoprenoid or polyisoprenoid alcohol. An example of a suitable carrier is dolichol phosphate. The oligosaccharide may be attached to a carrier via a labile bond allowing for chemical removal of the oligosaccharide from the lipid carrier. In the alternative, the oligosaccharide transferase may be used to transfer the oligosaccharide from a lipid carrier to a polypeptide.

The following examples are intended to further illustrate the invention without limiting its scope.

EXAMPLES

Recently, Nakayama et al. (Nakayama et al., 1999) reported the cloning of a novel human α4GlcNAc-transferase (SEQ ID NO:12) responsible for the synthesis of the structures GlcNAcα1-4Galβ1-4GlcNAcβ1-R and GlcNAcα1-4Galβ1-3GalNAcα1-R. The gene was mapped to chromosome 3p14.3. Since this is the first mammalian glycosyltransferase gene available which forms an α1-4 linkage, it was hypothesized that this gene would represent one member of a family of homologous glycosyltransferase genes. A characteristic feature of homologous glycosyltransferase genes is that different members may encode enzymes which have different donor or acceptor sugar specificities, but the nature of the linkage formed is often retained (Amado et al., 1999).

A sequence derived from a BAC clone containing an open reading frame of 1059 bp was predicted to represent a new gene (SEQ ID NO:10) encoding a $P^k$ α4Gal-T forming the Galα1-4Glc(NAc) linkages (SEQ ID NO:11). This report described the cloning and expression of this gene, designated α4Gal-T1, and demonstrates that the gene represent the $P^k$ gene and its encoded enzyme represents the $P^k$ synthase.

Example 1

Identification and Cloning of α4Gal-T1 tBLASTn analysis of the human genome survey sequences (GSS), unfinished High Throughput Genomic Sequences (HTG), and dbEST databases at The National Center for Biotechnology Information (NCBI, NIH, Bethesda, Md., USA) with the coding sequence of a human α4GlcNAc-transferase recently cloned (Nakayama et al., 1999), produced a novel open reading frame of 1059 bp with significant similarity (SEQ ID NO:10). The full coding sequence was available from BAC clone SC22CB-33B7 on chromosome 22 (GenBank accession number Z82176) in a single exon. With the release of the sequence of chromosome 22 the mapping data is cB33B7.1 at $2.65055 \times 10^7$ to $2.65044 \times 10^7$ flanked by Diaphorase (NADH) and an unknown protein. Linkage analysis of the $P_1$ polymorphism was originally performed with NADH-cytochrome b5 reductase (McAlpine et al., 1978). Few ESTs cover the coding region (e.g. R45869), but the 3'UTR is covered by EST Unigene cluster Hs.105956. Available ESTs are mainly derived from tonsil, prostate, and germ cell tumors.

Example 2

Identification of Sequence Polymorphisms in the Coding Region α4Gal-T1

The sequence analysis was performed in three steps. Initially, the coding region of α4Gal-T1 from seven $P_1$+, five $P_1$−, and six p phenotype individuals were sequenced in full by direct sequencing of a genomic fragment of 1295 bp derived by PCR with primer pair HCRS122 (5'-CCAGCCT-TGGCTCTGGCTGATG) (SEQ ID NO:1) and HCRS126 (5'-CCCTCACAAGTACATTTTCATG) (SEQ ID NO:2) located downstream and upstream of the translational start and stop sites, respectively. The PCR products were sequenced in both directions using the primers HCRS122, HCRS126, HCRS1 (5'-ATCTCACTTCTGAGCTGC) (SEQ ID NO:3) and HCRS4 (5'-GTTGTAGTGGTCCACGAAGTC) (SEQ ID NO:4). Subsequently, the products from two individuals (#194 and #321) homozygous for G109 and two (#183 and #300) homozygous for A109, randomly selected were subjected to cloning into pBluescript KS+ (Stratagene) followed by sequencing of clones. Finally, a genotyping assay based on RcaI restriction enzyme digestion of a PCR product was developed for the identified A109G missense mutation allele. PCR was performed using primer pair HCRS133 (5'-AAGCTCCTGGTCTGATCTGG) (SEQ ID NO:5) and HCRS6 (5'-ACCGAGCACATGCAGGAAGTT) (SEQ ID NO: 6) (30 cycles of 94° C. for 30 s, 58° C. for 30s, and 72° C. for 45 s), and a total of 31 $P_1+$ and 51 $P_1-$ phenotyped individuals was typed. RcaI digestion cleaves the expected product (319 bp) of A109 in two fragments of 182 and 137 bp. The RcaI digestion of PCR products was confirmed by Southern analysis on 3 $P_1+$ and 2 $P_1-$ individuals.

Example 3

Expression of α4Gal-T1 in Insect Cells

Full coding constructs were prepared by genomic PCR using primer pair HCRS131 (5'-ACCATGCCAAGC-CCCCCGACCTC) (SEQ ID NO:7) and HCRS125 (5'-CCCCTCACAAGACATTTTCATG) (SEQ ID NO:8) and genomic DNA from phenotyped individuals with phenotypes $P_1+$ (#165) and p (#4) (see Table II for sequence). Three different full coding constructs were selected for expression: #67 (A109, T548, G903, G987), #45 (G109, T548, G903, A987), and p#5 (A109, A548, G903, G987). The products were cloned into BamHI and EcoRI sites of pBluescript KS+, and subsequently into the insect cell expression vector pVL1393 (Pharmingen), and sequenced in full. A truncated, secreted construct (amino acid residues 46-353) was prepared using primer pair HCRS124 (5'-CCCAAG-GAGAAAGGGCAGCTC) (SEQ ID NO:9) and HCRS125 from a $P_1+$ phenotype individual (#165), and the sequence confirmed as described above. The products were cloned into the expression vector pAcGP67A (Pharmingen). The variants of plasmids pVL-α4Gal-T1-full and pAcGP67-α4Gal-T1-sol were co-transfected with Baculo-Gold™ DNA (Pharmingen), and virus amplified as described previously (Bennett et al., 1996). Standard assays were performed in 50 µl reaction mixtures containing 25 mM Cacodylate (pH 6.5), 10 mM $MnCl_2$, 0.25% Triton X-100, 100 µM UDP-[$^{14}$C]Gal (10,000 cpm/nmol) (Amersham), and the indicated concentrations of acceptor substrates (Sigma and Dextra Laboratories Ltd) (see Table I for structures). The full coding constructs were assayed with 1% Triton X-100 homogenates of cells twice washed in phosphate buffered saline or resuspended microsomal fractions.

Example 4

Expression of α4Gal-T1 in $P^k$ Negative Namalwa Cells

The three full coding constructs #67, #45, and p#5, were cloned into pDR2 (Clontech, USA). Insert was excised from pBKs with BamHI/XhoI and inserted into the BamHI/SalI sites of pDR2. Transient transfection of $5 \times 10^6$ Namalwa cells with 20 µg cDNA was done by double-pulse electroporation using an Easy-cell ject+ (Eurogentec, France). Expression of CD77/$P^k$ antigen was evaluated by FACS analysis on a FACSCalibur (Beckton-Dickinson, USA) using 1A4 monoclonal antibody (Wiels, 1997).

Example 5

Characterisation of the Product Formed with α4Gal-T1

For product characterization 2 mg CDH was glycosylated with a microsomal fraction of High Five cells infected with pVL-α4Gal-T1-full (#67) using thin-layer-chromatography to monitor reaction progress. The reaction products were purified on an octadecyl-silica cartridge (Bakerbond, J. T. Baker, USA), deuterium exchanged by repeated addition of $CDCl_3$-$CD_3OD$ 2:1, sonication, and evaporation under dry nitrogen, and then dissolved in 0.5 mL DMSO-$d_6$/2% $D_2O$ (Dabrowski et al., 1980) (containing 0.03% tetramethylsilane as chemical shift reference) for NMR analysis. 1-D $^1$H-NMR spectra were acquired at 35° C. on a Varian Inova 600 MHz spectrometer; 1200 FIDs were accumulated, with solvent suppression by presaturation pulse during the relaxation delay. Spectra were interpreted by comparison to those of relevant glycosphingolipid standards acquired under virtually identical conditions, as well as to previously published data for which a somewhat different temperature (65° C.) was employed (Dabrowski et al., 1980; Kannagi et al., 1983).

Example 6

Northern Analysis of α4Gal-T1

The cDNA-fragment of full coding α4Gal-T1 (#67) was used as probe. The probe was random priming labeled using [α32P]dCTP and a Strip-EZ DNA labeling kit (Ambion). Multiple tissue northern (MTN-H12) blot was obtained from Clontech. Eight human cell lines (Ramos, MutuI, BL2, Namalwa, Remb1, 8866, T51 and K562) were analysed because pk synthase activity and antigen expression have been characterized previously (Taga et al., 1995b; Taga et al., 1995a). Total cellular RNA was extracted from cell lines using the RNeasy midi kit (Qiagen SA, France).

REFERENCES

Almeida, R., Amado, M., David, L., et al. A Family of Human β4-Galactosyltransferases: Cloning and expression of two novel UDP-Galactose: β-N-Acetylglucosamine β1,4-Galactosyltransferases, β4Gal-T2 and β4Gal-T3. *J. Biol. Chem.* 272:31979-31992, 1997.

Amado, M., Almeida, R., Schwientek, T. and Clausen, H. Identification and Characterization of Large Galactosyltransferase Gene Families: Galactosyltransferases for all functions. *Biochim Biophys Acta* in press:1999.

Bailly, P. and Bouhors, J.-P. P Blood Group and Related Antigens. In: *Blood Cell Biochemistry*, edited by Cartron, J. and Rouger, P. Plenum Press, 1995, p. 299-329.

Bailly, P., Piller, F., Gillard, B., Veyrieres, A., Marcus, D. and Cartron, J. P. Biosynthesis of the blood group Pk and P1 antigens by human kidney microsomes. *Carbohydr. Res* 228:277-287, 1992.

Bennett, E. P., Hassan, H. and Clausen, H. cDNA cloning and expression of a novel human UDP-N-acetyl-alpha-D-galactosamine. Polypeptide N-acetylgalactosaminyltransferase, GalNAc-t3. *J. Biol. Chem.* 271:17006-17012, 1996.

Bennett, E. P., Hassan, H., Mandel, U., et al. Cloning of a human UDP-N-acetyl-☐-D-galactosamine: polypeptide N-acetylgalactosaminyltransferase that complements other GalNAc-transferases in complete O-glycosylation of the MUC1 tandem repeat, *J. Biol. Chem.* 273:30472-30481, 1998.

Brew, K., Vanaman, T. C. and Hill, R. L. The role of alpha-lactalbumin and the A protein in lactose synthetase: a unique mechanism for the control of a biological reaction. *Proc Natl Acad Sci USA* 59:491-497, 1968.

Brodbeck, U., Denton, W. L., Tanahashi, N. and Ebner, K. E. The isolation and identification of the B protein of lactose synthetase as alpha-lactalbumin. *J. Biol. Chem.* 242:1391-1397, 1967.

Cedergren, B. Population studies in northern Sweden. IV. Frequency of the blood type p. *Hereditas* 73:27-30, 1973.

Charron, M., Shaper, J. H. and Shaper, N. L. The increased level of beta1,4-galactosyltransferase required for lactose biosynthesis is achieved in part by translational control. *Proc Natl Acad Sci U.S.A* 95:14805-14810, 1998.

Clausen, H. and Hakomori, S. ABH and related histo-blood group antigens; immunochemical differences in carrier isotypes and their distribution. *Vox Sanguinis* 56:1-20, 1989.

Dabrowski, J., Hanfland, P. and Egge, H. Structural analysis of glycosphingolipids by high resolution 1H nuclear magnetic resonance spectroscopy. *Biochemistry* 19:5652-5658, 1980.

Daniels, G. L., Anstee, D. J., Cartron, J. P., et al. Terminology for red cell surface antigens. ISBT Working Party Oslo Report. International Society of Blood Transfusion. *Vox Sang.* 77:52-57, 1999.

Do, K. Y., Do, S. I. and Cummings, R. D. Alpha-lactalbumin induces bovine milk beta 1,4-galactosyltransferase to utilize UDP-GalNAc. *J. Biol. Chem.* 270:18447-18451, 1995.

Fletcher, K. S., Bremer, E. G. and Schwarting, G.A.P blood group regulation of glycosphingolipid levels in human erythrocytes. *J Biol Chem.* 254:11196-11198, 1979.

Gotschlich, E. C. Genetic locus for the biosynthesis of the variable portion of *Neisseria gonorrhoeae* lipooligosaccharide. *J Exp. Med.* 180:2181-2190, 1994.

Iizuka, S., Chen, S. H. and Yoshida, A. Studies on the human blood group P system: an existence of UDP-Gal:lactosylceramide alpha 1- - - 4 galactosyltransferase in the small p type cells. *Biochem Biophys Res Commun.* 137:1187-1195, 1986.

Issitt, P. D. and Anstee, D. J. The P Blood Group System and the Antigens P, pk and LKE. In: *Applied Blood Group Serology*, AnonymousMontgomery Sci. Publ., 1998, p. 295-313.

Kannagi, R., Levery, S. B., Ishigami, F., et al. New globosides glycosphingolipids in human teratocarcinoma reactive with the monoclonal antibody directed to a developmentally regulated antigen, stage-specific embryonic antigen 3. *J. Biol. Chem.* 258:8934-8942, 1983.

Karlsson, K. A. Meaning and therapeutic potential of microbial recognition of host glycoconjugates. *Mol. Microbiol.* 29:1-11, 1998.

Kelly, R. J., Ernst, L. K., Larsen, R. D., Bryant, J. G., Robinson, J. S. and Lowe, J. B. Molecular basis for H blood group deficiency in Bombay (Oh) and para-Bombay individuals. *Proc Natl Acad Sci U.S.A* 91:5843-5847, 1994.

Kelly, R. J., Rouquier, S., Giorgi, D., Lennon, G. G. and Lowe, J. B. Sequence and expression of a candidate for the human Secretor blood group alpha(1,2)fucosyltransferase gene (FUT2). Homozygosity for an enzyme-inactivating nonsense mutation commonly correlates with the non-secretor phenotype. *J Biol Chem.* 270:4640-4649, 1995.

Kozak, M. Structural features in eukaryotic mRNAs that modulate the initiation of translation. *J. Biol. Chem.* 266:19867-19870, 1991.

Landsteiner, K. and Levine, P. *Proc. Soc. Biol. Exp. Biol. N.Y.* 24:9411927.

Lopez, M., Gazon, M., Juliant, S., et al. Characterization of a UDP-Gal:Galbetal-3GalNAc alpha1, 4-galactosyltransferase activity in a Mamestra brassicae cell line. *J Biol Chem.* 273:33644-33651, 1998.

Mandel, U., Hassan, H., Therkildsen, M. H., et al. Expression of polypeptide GalNAc-transferases in stratified epithelia and squamous cell carcinomas: immunohistological evaluation using monoclonal antibodies to three members of the GalNAc-transferase family. *Glycobiology* 9:43-52, 1999.

Mangeney, M., Lingwood, C. A., Taga, S., Caillou, B., Tursz, T. and Wiels, J. Apoptosis induced in Burkitt's lymphoma cells via Gb3/CD77, a glycolipid antigen. *Cancer Res* 53:5314-5319, 1993.

Marcus, D. M. The Ii and P blood group systems. *Immunol. Ser.* 43:701-712, 1989.

Marcus, D. M. and Kundu, S. K. Immunochemistry of the P blood group system. *Prog. Clin. Biol Res* 43:55-65, 1980.

Martin, S. L., Edbrooke, M. R., Hodgman, T. C., Van den Eijnden, D. H. and Bird, M. I. Lewis X biosynthesis in *Helicobacter pylori*. Molecular cloning of an alpha(1,3)-fucosyltransferase gene. *J. Biol. Chem.* 272:21349-21356, 1997.

McAlpine, P. J., Kaita, H. and Lewis, M. Is the DIA1 locus linked to the P blood group locus? *Cytogenet. Cell Genet.* 22:629-632, 1978.

Mollicone, R., Reguigne, I., Kelly, R. J., et al. Molecular basis for Lewis alpha(1,3/1,4)-fucosyltransferase gene deficiency (FUT3) found in Lewis-negative Indonesian pedigrees. *J Biol Chem.* 269:20987-20994, 1994.

Naiki, M., Fong, J., Ledeen, R. and Marcus, D. M. Structure of the human erythrocyte blood group P1 glycosphingolipid. *Biochemistry* 14:4831-4837, 1975.

Naiki, M. and Marcus, D. M. Human erythrocyte P and Pk blood group antigens: identification as glycosphingolipids. *Biochem Biophys Res Commun.* 60:1105-1111, 1974.

Nakayama, J., Yeh, J. C., Misra, A. K., Ito, S., Katsuyama, T. and Fukuda, M. Expression cloning of a human alpha1, 4-N-acetylglucosaminyltransferase that forms GlcNAcalpha1-->4Galbeta-->R, a glycan specifically expressed in the gastric gland mucous cell-type mucin. *Proc Natl Acad Sci U.S.A* 96:8991-8996, 1999.

Nishihara, S., Narimatsu, H., Iwasaki, H., et al. Molecular genetic analysis of the human Lewis histo-blood group system. *J Biol Chem.* 269:29271-29278, 1994.

Paulson, J. C. and Colley, K. J. Glycosyltransferases. Structure, localization, and control of cell type-specific glycosylation. *J. Biol. Chem.* 264:17615-17618, 1989.

Puri, A., Hug, P., Jernigan, K., Rose, P. and Blumenthal, R. Role of glycosphingolipids in HIV-1 entry: requirement of globotriosylceramide (Gb3) in CD4/CXCR4-dependent fusion. *Biosci. Rep.* 19:317-325, 1999.

Sasaki, K., Kurata-Miura, K., Ujita, M., et al. Expression cloning of cDNA encoding a human beta-1,3-N-acetylglucosaminyltransferase that is essential for poly-N-acetyllactosamine synthesis. *Proc Natl Acad Sci U.S.A* 94:14294-14299, 1997.

Taga, S., Carlier, K., Mishal, Z., et al. Intracellular signaling events in CD77-mediated apoptosis of Burkitt's lymphoma cells. *Blood* 90:2757-2767, 1997.

Taga, S., Mangeney, M., Tursz, T. and Wiels, J. Differential regulation of glycosphingolipid biosynthesis in phenotypically distinct Burkitt's lymphoma cell lines. *Int. J Cancer* 61:261-267, 1995a.

Taga, S., Tetaud, C., Mangeney, M., Tursz, T. and Wiels, J. Sequential changes in glycolipid expression during human B cell differentiation: enzymatic bases. *Biochim Biophys Acta* 1254:56-65, 1995b.

Tippett, P., Andrews, P. W., Knowles, B. B., Solter, D. and Goodfellow, P. N. Red cell antigens P (globoside) and Luke: identification by monoclonal antibodies defining the murine stage-specific embryonic antigens-3 and -4 (SSEA-3 and SSEA-4). *Vox Sang.* 51:53-56, 1986.

Wakarchuk, W. W., Cunningham, A., Watson, D. C. and Young, N. M. Role of paired basic residues in the expression of active recombinant galactosyltransferases from the bacterial pathogen *Neisseria meningitidis*. *Protein Eng.* 11:295-302, 1998.

Watkins, W. M. Biochemistry and Genetics of the ABO, Lewis, and P blood group systems. *Adv. Hum. Genet.* 10:1-136, 1980.

Wiels, J. CD77 Final Workshop. In: *Leukocyte Typing VI*, edited by Kishimoto, T. London: Garland Publishing Inc., 1997, p. 175-177.

Wiels, J., Taga, S., Tetaud, C., Cedergren, B., Nilsson, B. and Clausen, H. Histo-blood group p: biosynthesis of globoseries glycolipids in EBV-transformed B cell lines. *Glycoconj. J* 13:529-535, 1996.

Wiggins, C. A. R. and Munro, S. Activity of the yeast MNN1alfa-1,3-mannosyltransferase requires a motif conserved in many other families of glycosyltransferases. *Proc. Natl. Acad. Sci. USA* 95:7945-7950, 1998.

Yamamoto, F., Clausen, H., White, T., Marken, J. and Hakomori, S. Molecular genetic basis of the histo-blood group ABO system. *Nature* 345:229-233, 1990.

Yoshida, H., Ito, K., Kusakari, T., et al. Removal of maternal antibodies from a woman with repeated fetal loss due to P blood group incompatibility. *Transfusion* 34:702-705, 1994.

Zhou, D., Dinter, A., Gutierrez, G. R., et al. A beta-1,3-N-acetylglucosaminyltransferase with poly-N-acetyllactosamine synthase activity is structurally related to beta-1,3-galactosyltransferases. *Proc Natl Acad Sci U.S.A* 96:406-411, 1999.

---

What is claimed is:

1. An isolated polypeptide comprising amino acids 46-353 of SEQ ID NO: 11, said polypeptide having UDP-galactose: β-D-galactose-R4-α-D-galactosyltransferase (α4Gal-T1) enzyme activity.

2. An isolated polypeptide comprising an amino acid sequence at least 95% identical to amino acids 46-353 of SEQ ID NO: 11, said polypeptide having UDP-galactose: β-D-galactose-R4-α-D-galactosyltransferase (α4Gal-T1) enzyme activity.

3. A polypeptide prepared in accordance with a method comprising:
   (a) introducing into a host cell a nucleic acid encoding a polypeptide with UDP-galactose: βD-galactose-R4-α-D-galactosyltransferase (α4Gal-T1) enzyme activity;
   (b) growing the host cell under conditions suitable for expression of the polypeptide; and
   (c) isolating the polypeptide produced by the host cell, wherein the polypeptide with α4Gal-T1 enzyme activity is selected from the group consisting of:
   (i) a polypeptide comprising amino acids 46-353 of SEQ ID NO: 11; and
   (ii) a polypeptide comprising an amino acid sequence at least 95% identical to amino acids 46-353 of SEQ ID NO: 11.

4. A method for preparing an oligosaccharide comprising contacting a reaction mixture comprising a donor substrate and an acceptor substrate in the presence of the polypeptide of claim 1.

5. A method for preparing an oligosaccharide comprising contacting a reaction mixture comprising a donor substrate and an acceptor substrate in the presence of the polypeptide of claim 2.

6. A method for preparing an oligosaccharide comprising contacting a reaction mixture comprising a donor substrate and an acceptor substrate in the presence of the polypeptide of claim 3.

7. A composition comprising the polypeptide of claim 1 and a pharmaceutically acceptable carrier, excipient or diluent.

8. A composition comprising the polypeptide of claim 2 and a pharmaceutically acceptable carrier, excipient or diluent.

9. A composition comprising the polypeptide of claim 3 and a pharmaceutically acceptable carrier, excipient or diluent.

10. An isolated polypeptide consisting of amino acids 46-353 of SEQ ID NO: 11.

11. An isolated polypeptide consisting of an amino acid sequence at least 95% identical to amino acids 46-353 of SEQ ID NO: 11, said polypeptide having with UDP-galactose: β-D-galactose-R4-β-D-galactosyltransferase (β4Gal-T1) enzyme activity.

* * * * *

SEQUENCE LISTING

```
<160> NUMBER OF SEQ ID NOS: 13

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 1
ccagccttgg ctctggctga tg                                              22

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 2
ccctcacaag tacattttca tg                                              22

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 3
atctcacttc tgagctgc                                                   18

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 4
```

```
gttgtagtgg tccacgaagt c                                              21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
aagctcctgg tctgatctgg                                                20

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
accgagcaca tgcaggaagt t                                              21

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 7
accatgccaa gcccccgac ctc                                             23

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 8
cccctcacaa gacattttca tg                                             22

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 9
cccaaggaga aagggcagct c                                              21

<210> SEQ ID NO 10
<211> LENGTH: 1059
<212> TYPE: DNA
<213> ORGANISM: Homo sapiens
<220> FEATURE:
<221> NAME/KEY: CDS
<222> LOCATION: (1)..(1059)
<223> OTHER INFORMATION: human alpha4Gal-T1

<400> SEQUENCE: 10 atg tcc aag ccc ccc gac ctc ctg ctg cgg ctg ctc cgg ggc gcc cca    48
Met Ser Lys Pro Pro Asp Leu Leu Leu Arg Leu Leu Arg Gly Ala Pro
 1               5                  10                  15
```

```
agg cag cgg gtc tgc acc ctg ttc atc atc ggc ttc aag ttc acg ttt      96
Arg Gln Arg Val Cys Thr Leu Phe Ile Ile Gly Phe Lys Phe Thr Phe
            20                  25                  30 ttc gtc tcc atc atg atc tac tgg cac gtt gtg gga gag ccc aag gag     144
Phe Val Ser Ile Met Ile Tyr Trp His Val Val Gly Glu Pro Lys Glu
        35                  40                  45 aaa ggg cag ctc tat aac ctg cca gca gag atc ccc tgc ccc acc ttg     192
Lys Gly Gln Leu Tyr Asn Leu Pro Ala Glu Ile Pro Cys Pro Thr Leu
    50                  55                  60 aca ccc ccc acc cca ccc tcc cac ggc ccc act cca ggc aac atc ttc     240
Thr Pro Pro Thr Pro Pro Ser His Gly Pro Thr Pro Gly Asn Ile Phe
65                  70                  75                  80 ttc ctg gag act tca gac cgg acc aac ccc aac ttc ctg ttc atg tgc     288
Phe Leu Glu Thr Ser Asp Arg Thr Asn Pro Asn Phe Leu Phe Met Cys
                85                  90                  95 tcg gtg gag tcg gcc gcc aga act cac ccc gaa tcc cac gtg ctg gtc     336
Ser Val Glu Ser Ala Ala Arg Thr His Pro Glu Ser His Val Leu Val
            100                 105                 110 ctg atg aaa ggg ctt ccg ggt ggc aac gcc tct ctg ccc cgg cac ctg     384
Leu Met Lys Gly Leu Pro Gly Gly Asn Ala Ser Leu Pro Arg His Leu
        115                 120                 125 ggc atc tca ctt ctg agc tgc ttc ccg aat gtc cag atg ctc ccg ctg     432
Gly Ile Ser Leu Leu Ser Cys Phe Pro Asn Val Gln Met Leu Pro Leu
    130                 135                 140 gac ctg cgg gag ctg ttc cgg gac aca ccc ctg gcc gac tgg tac gcg     480
Asp Leu Arg Glu Leu Phe Arg Asp Thr Pro Leu Ala Asp Trp Tyr Ala
145                 150                 155                 160 gcc gtg cag ggg cgc tgg gag ccc tac ctg ctg ccc gtg ctc tcc gac     528
Ala Val Gln Gly Arg Trp Glu Pro Tyr Leu Leu Pro Val Leu Ser Asp
                165                 170                 175 gcc tcc agg atc gca ctc atg tgg aag ttc ggc ggc atc tac ctg gac     576
Ala Ser Arg Ile Ala Leu Met Trp Lys Phe Gly Gly Ile Tyr Leu Asp
            180                 185                 190 acg gac ttc att gtt ctc aag aac ctg cgg aac ctg acc aac gtg ctg     624
Thr Asp Phe Ile Val Leu Lys Asn Leu Arg Asn Leu Thr Asn Val Leu
        195                 200                 205 ggc acc cag tcc cgc tac gtc ctc aac ggc gcg ttc ctg gcc ttc gag     672
Gly Thr Gln Ser Arg Tyr Val Leu Asn Gly Ala Phe Leu Ala Phe Glu
    210                 215                 220 cgc cgg cac gag ttc atg gcg ctg tgc atg cgg gac ttc gtg gac cac     720
Arg Arg His Glu Phe Met Ala Leu Cys Met Arg Asp Phe Val Asp His
225                 230                 235                 240 tac aac ggc tgg atc tgg ggt cac cag ggc ccg cag ctg ctc acg cgg     768
Tyr Asn Gly Trp Ile Trp Gly His Gln Gly Pro Gln Leu Leu Thr Arg
                245                 250                 255 gtc ttc aag aag tgg tgt tcc atc cgc agc ctg gcc gag agc cgc gcc     816
Val Phe Lys Lys Trp Cys Ser Ile Arg Ser Leu Ala Glu Ser Arg Ala
            260                 265                 270 tgc cgc ggc gtc acc acc ctg ccc cct gag gcc ttc tac ccc atc ccc     864
Cys Arg Gly Val Thr Thr Leu Pro Pro Glu Ala Phe Tyr Pro Ile Pro
        275                 280                 285 tgg cag gac tgg aag aag tac ttt gag gac atc aac ccc gag gag ctg     912
Trp Gln Asp Trp Lys Lys Tyr Phe Glu Asp Ile Asn Pro Glu Glu Leu
    290                 295                 300 ccg cgg ctg ctc agt gcc acc tat gct gtc cac gtg tgg aac aag aag     960
Pro Arg Leu Leu Ser Ala Thr Tyr Ala Val His Val Trp Asn Lys Lys
305                 310                 315                 320 agc cag ggc acg cgg ttc gag gcc acg tcc agg gca ctg ctg gcc cag    1008
Ser Gln Gly Thr Arg Phe Glu Ala Thr Ser Arg Ala Leu Leu Ala Gln
                325                 330                 335
```

```
ctg cat gcc cgc tac tgc ccc acg acg cac gag gcc atg aaa atg tac        1056
Leu His Ala Arg Tyr Cys Pro Thr Thr His Glu Ala Met Lys Met Tyr
        340                 345                 350 ttg                                                                    1059
Leu
```

<210> SEQ ID NO 11
<211> LENGTH: 353
<212> TYPE: PRT
<213> ORGANISM: Homo sapiens

<400> SEQUENCE: 11

```
Met Ser Lys Pro Pro Asp Leu Leu Arg Leu Leu Arg Gly Ala Pro
 1               5                  10                  15

Arg Gln Arg Val Cys Thr Leu Phe Ile Ile Gly Phe Lys Thr Phe
                20                  25                  30

Phe Val Ser Ile Met Ile Tyr Trp His Val Val Gly Glu Pro Lys Glu
                35                  40                  45

Lys Gly Gln Leu Tyr Asn Leu Pro Ala Glu Ile Pro Cys Pro Thr Leu
     50                  55                  60

Thr Pro Pro Thr Pro Pro Ser His Gly Pro Thr Pro Gly Asn Ile Phe
 65                  70                  75                  80

Phe Leu Glu Thr Ser Asp Arg Thr Asn Pro Asn Phe Leu Phe Met Cys
                 85                  90                  95

Ser Val Glu Ser Ala Ala Arg Thr His Pro Glu Ser His Val Leu Val
                100                 105                 110

Leu Met Lys Gly Leu Pro Gly Gly Asn Ala Ser Leu Pro Arg His Leu
            115                 120                 125

Gly Ile Ser Leu Leu Ser Cys Phe Pro Asn Val Gln Met Leu Pro Leu
        130                 135                 140

Asp Leu Arg Glu Leu Phe Arg Asp Thr Pro Leu Ala Asp Trp Tyr Ala
145                 150                 155                 160

Ala Val Gln Gly Arg Trp Glu Pro Tyr Leu Leu Pro Val Leu Ser Asp
                165                 170                 175

Ala Ser Arg Ile Ala Leu Met Trp Lys Phe Gly Gly Ile Tyr Leu Asp
            180                 185                 190

Thr Asp Phe Ile Val Leu Lys Asn Leu Arg Asn Leu Thr Asn Val Leu
        195                 200                 205

Gly Thr Gln Ser Arg Tyr Val Leu Asn Gly Ala Phe Leu Ala Phe Glu
    210                 215                 220

Arg Arg His Glu Phe Met Ala Leu Cys Met Arg Asp Phe Val Asp His
225                 230                 235                 240

Tyr Asn Gly Trp Ile Trp Gly His Gln Gly Pro Gln Leu Leu Thr Arg
                245                 250                 255

Val Phe Lys Lys Trp Cys Ser Ile Arg Ser Leu Ala Glu Ser Arg Ala
            260                 265                 270

Cys Arg Gly Val Thr Thr Leu Pro Pro Glu Ala Phe Tyr Pro Ile Pro
        275                 280                 285

Trp Gln Asp Trp Lys Lys Tyr Phe Glu Asp Ile Asn Pro Glu Glu Leu
    290                 295                 300

Pro Arg Leu Leu Ser Ala Thr Tyr Ala Val His Val Trp Asn Lys Lys
305                 310                 315                 320

Ser Gln Gly Thr Arg Phe Glu Ala Thr Ser Arg Ala Leu Leu Ala Gln
                325                 330                 335
```

```
Leu His Ala Arg Tyr Cys Pro Thr Thr His Glu Ala Met Lys Met Tyr
            340                 345                 350

Leu

<210> SEQ ID NO 12
<211> LENGTH: 1020
<212> TYPE: DNA
<213> ORGANISM: Homo sapiens
<220> FEATURE:
<221> NAME/KEY: CDS
<222> LOCATION: (1)..(1020)
<223> OTHER INFORMATION: alpha4GlcNAc-T

<400> SEQUENCE: 12 atg cgg aag gag ctc cag ctc tcc ctg tca gtc acc ttg ctg ctt gtc      48
Met Arg Lys Glu Leu Gln Leu Ser Leu Ser Val Thr Leu Leu Leu Val
  1               5                  10                  15 tgt ggc ttc ctc tac cag ttc acc ctg aag tcc agc tgc ctc ttc tgt      96
Cys Gly Phe Leu Tyr Gln Phe Thr Leu Lys Ser Ser Cys Leu Phe Cys
                 20                  25                  30 ttg cct tct ttc aag tcc cac cag ggg ctg gaa gcc ctc ctg agc cac     144
Leu Pro Ser Phe Lys Ser His Gln Gly Leu Glu Ala Leu Leu Ser His
             35                  40                  45 aga cgt ggc att gtg ttt cta gag acc tca gag aga atg gag cca ccc     192
Arg Arg Gly Ile Val Phe Leu Glu Thr Ser Glu Arg Met Glu Pro Pro
         50                  55                  60 cat ttg gtc tcc tgt tcc gta gag tct gct gcc aag att tat cct gag     240
His Leu Val Ser Cys Ser Val Glu Ser Ala Ala Lys Ile Tyr Pro Glu
 65                  70                  75                  80 tgg cct gtg gtg ttc ttt atg aag ggt ctt act gat tcc aca ccg atg     288
Trp Pro Val Val Phe Phe Met Lys Gly Leu Thr Asp Ser Thr Pro Met
                 85                  90                  95 ccc tca aac tcc aca tac cca gct ttt tcc ttc ctg tca gca ata gac     336
Pro Ser Asn Ser Thr Tyr Pro Ala Phe Ser Phe Leu Ser Ala Ile Asp
            100                 105                 110 aac gtt ttc ctc ttc cct ttg gat atg aaa agg ctg ctt gaa gac aca     384
Asn Val Phe Leu Phe Pro Leu Asp Met Lys Arg Leu Leu Glu Asp Thr
        115                 120                 125 cca ttg ttt tca tgg tac aat caa atc aac gcc agc gca gag aga aac     432
Pro Leu Phe Ser Trp Tyr Asn Gln Ile Asn Ala Ser Ala Glu Arg Asn
    130                 135                 140 tgg ctc cac atc agc tcg gat gca tcc cgc ctg gcc atc atc tgg aaa     480
Trp Leu His Ile Ser Ser Asp Ala Ser Arg Leu Ala Ile Ile Trp Lys
145                 150                 155                 160 tac ggt ggc atc tac atg gac acc gat gtc atc tcc atc agg ccc atc     528
Tyr Gly Gly Ile Tyr Met Asp Thr Asp Val Ile Ser Ile Arg Pro Ile
                165                 170                 175 cct gag gag aac ttt ttg gct gcg cag gct tct cgg tac tct agt aat     576
Pro Glu Glu Asn Phe Leu Ala Ala Gln Ala Ser Arg Tyr Ser Ser Asn
            180                 185                 190 gga ata ttt ggg ttc ctc ccc cac cac ccc ttt ttg tgg gaa tgc atg     624
Gly Ile Phe Gly Phe Leu Pro His His Pro Phe Leu Trp Glu Cys Met
        195                 200                 205 gaa aac ttt gtt gaa cac tat aat tca gcc att tgg ggc aac caa ggc     672
Glu Asn Phe Val Glu His Tyr Asn Ser Ala Ile Trp Gly Asn Gln Gly
    210                 215                 220 cct gag ttg atg aca agg atg ttg agg gta tgg tgt aaa ctt gaa gac     720
Pro Glu Leu Met Thr Arg Met Leu Arg Val Trp Cys Lys Leu Glu Asp
225                 230                 235                 240 ttc cag gag gtg agc gac ctc agg tgt ctg aac ata tcc ttc tta cac     768
Phe Gln Glu Val Ser Asp Leu Arg Cys Leu Asn Ile Ser Phe Leu His
```

```
                    245                 250                 255
ccc caa aga ttt tac ccc atc tcc tat cga gag tgg agg cgc tac tat      816
Pro Gln Arg Phe Tyr Pro Ile Ser Tyr Arg Glu Trp Arg Arg Tyr Tyr
            260                 265                 270 gaa gtg tgg gat aca gag cca agc ttc aat gtc tct tat gcc ctg cat      864
Glu Val Trp Asp Thr Glu Pro Ser Phe Asn Val Ser Tyr Ala Leu His
            275                 280                 285 ttg tgg aac cac atg aac cag gag ggg cgg gct gtg att aga gga agc      912
Leu Trp Asn His Met Asn Gln Glu Gly Arg Ala Val Ile Arg Gly Ser
        290                 295                 300 aac aca ctg gtg gaa aat ctc tat cgc aag cac tgt ccc agg act tac      960
Asn Thr Leu Val Glu Asn Leu Tyr Arg Lys His Cys Pro Arg Thr Tyr
305                 310                 315                 320 agg gac ctg att aaa ggc cca gag ggg tca gtg act ggg gag ctg ggt     1008
Arg Asp Leu Ile Lys Gly Pro Glu Gly Ser Val Thr Gly Glu Leu Gly
                325                 330                 335 cca ggt aac aaa                                                     1020
Pro Gly Asn Lys
            340

<210> SEQ ID NO 13
<211> LENGTH: 340
<212> TYPE: PRT
<213> ORGANISM: Homo sapiens

<400> SEQUENCE: 13

Met Arg Lys Glu Leu Gln Leu Ser Leu Ser Val Thr Leu Leu Leu Val
1               5                   10                  15

Cys Gly Phe Leu Tyr Gln Phe Thr Leu Lys Ser Ser Cys Leu Phe Cys
                20                  25                  30

Leu Pro Ser Phe Lys Ser His Gln Gly Leu Glu Ala Leu Leu Ser His
            35                  40                  45

Arg Arg Gly Ile Val Phe Leu Glu Thr Ser Glu Arg Met Glu Pro Pro
        50                  55                  60

His Leu Val Ser Cys Ser Val Glu Ser Ala Ala Lys Ile Tyr Pro Glu
65                  70                  75                  80

Trp Pro Val Val Phe Met Lys Gly Leu Thr Asp Ser Thr Pro Met
                85                  90                  95

Pro Ser Asn Ser Thr Tyr Pro Ala Phe Ser Phe Leu Ser Ala Ile Asp
            100                 105                 110

Asn Val Phe Leu Phe Pro Leu Asp Met Lys Arg Leu Leu Glu Asp Thr
        115                 120                 125

Pro Leu Phe Ser Trp Tyr Asn Gln Ile Asn Ala Ser Ala Glu Arg Asn
130                 135                 140

Trp Leu His Ile Ser Ser Asp Ala Ser Arg Leu Ala Ile Trp Lys
                150                 155                 160
145

Tyr Gly Gly Ile Tyr Met Asp Thr Asp Val Ile Ser Ile Arg Pro Ile
            165                 170                 175

Pro Glu Glu Asn Phe Leu Ala Ala Gln Ala Ser Arg Tyr Ser Ser Asn
        180                 185                 190

Gly Ile Phe Gly Phe Leu Pro His His Pro Phe Leu Trp Glu Cys Met
    195                 200                 205

Glu Asn Phe Val Glu His Tyr Asn Ser Ala Ile Trp Gly Asn Gln Gly
        210                 215                 220

Pro Glu Leu Met Thr Arg Met Leu Arg Val Trp Cys Lys Leu Glu Asp
225                 230                 235                 240
```

```
                                        -continued
Phe Gln Glu Val Ser Asp Leu Arg Cys Leu Asn Ile Ser Phe Leu His
                245                 250                 255

Pro Gln Arg Phe Tyr Pro Ile Ser Tyr Arg Glu Trp Arg Arg Tyr Tyr
                260                 265                 270

Glu Val Trp Asp Thr Glu Pro Ser Phe Asn Val Ser Tyr Ala Leu His
            275                 280                 285

Leu Trp Asn His Met Asn Gln Glu Gly Arg Ala Val Ile Arg Gly Ser
        290                 295                 300

Asn Thr Leu Val Glu Asn Leu Tyr Arg Lys His Cys Pro Arg Thr Tyr
305                 310                 315                 320

Arg Asp Leu Ile Lys Gly Pro Glu Gly Ser Val Thr Gly Glu Leu Gly
                325                 330                 335

Pro Gly Asn Lys
            340
```